(12) United States Patent
Lo et al.

(10) Patent No.: US 7,790,170 B2
(45) Date of Patent: Sep. 7, 2010

(54) MODIFIED LEUKOTOXIN PROTEIN

(75) Inventors: Reggie Y. C. Lo, Guelph (CA); Patricia E. Shewen, Guelph (CA); Raymond W. H. Lee, Guelph (CA); Doug Hodgins, Milverton (CA); Judith N. Strommer, Guelph (CA)

(73) Assignee: University of Guelph, Guelph, Ontario (CA)

(*) Notice: Subject to any disclaimer, the term of this patent is extended or adjusted under 35 U.S.C. 154(b) by 114 days.

(21) Appl. No.: 11/877,134

(22) Filed: Oct. 23, 2007

(65) Prior Publication Data

US 2008/0138355 A1    Jun. 12, 2008

Related U.S. Application Data

(62) Division of application No. 10/148,884, filed as application No. PCT/CA00/01498 on Dec. 15, 2000, now Pat. No. 7,304,151.

(60) Provisional application No. 60/172,148, filed on Dec. 17, 1999.

(51) Int. Cl.
| | |
|---|---|
| *A61K 39/385* | (2006.01) |
| *C12N 15/12* | (2006.01) |
| *C12N 15/63* | (2006.01) |
| *C12N 1/21* | (2006.01) |
| *C12N 5/10* | (2006.01) |
| *C12N 15/82* | (2006.01) |
| *C07K 14/745* | (2006.01) |

(52) U.S. Cl. ............... 424/185.1; 424/184.1; 530/350; 530/380; 530/387.9

(58) Field of Classification Search .............. None
See application file for complete search history.

(56) References Cited

U.S. PATENT DOCUMENTS

| | | | |
|---|---|---|---|
| 5,143,830 | A | 9/1992 | Holland et al. |
| 5,336,491 | A | 8/1994 | Berget et al. |
| 5,476,657 | A | 12/1995 | Potter |
| 5,849,531 | A | 12/1998 | Potter |
| 5,871,750 | A | 2/1999 | Potter |

FOREIGN PATENT DOCUMENTS

| | | |
|---|---|---|
| CA | 2014033 | 10/1990 |
| WO | WO 98/46260 | 10/1998 |
| WO | WO 99/15670 | 4/1999 |

OTHER PUBLICATIONS

Cruz, W.T. et al.: "Deletion analysis resolves cell-binding and lytic domains of the *Pasteurella* leukotoxin" Mol. Microbiol., vol. 4, No. 11, 1990, pp. 1993-1939, XP000993015.

Tatum, F. M. et al.: "Construction of an isogenic leukotoxin deletion mutant of *Pasteurella haemolytica* serotype 1: characterization and virulence" Microbial Pathogenesis, vol. 24, 1998, pp. 37-46, XP000993013.

Bowie et al. "Deciphering the Message in Protein Sequences: Tolerance to Amino Acid Substitutions" Science, 1990, 257:1306-1310.

Greenspan et al. "Defining epitopes: It's not as easy as it seems" Nature Biotechnology 7:936-937, 1999.

Lee et al. "Towards Development of an Edible Vaccine against Bovine Pneumonic Pasteurellosis Using Transgenic White Clover Expressing a *Mannheimia haemolytica* A1 Leukotoxin 50 Fusion Protein", Infection and Immunity, 2001, vol. 69, No. 9, p. 5786-5793.

*Primary Examiner*—Robert A Zeman
(74) *Attorney, Agent, or Firm*—Bereskin & Parr LLP; Micheline Gravelle

(57) ABSTRACT

The present invention provides nucleic acid sequences encoding a modified leukotoxin protein, wherein the modification comprises the removal of nucleic acid sequences encoding amino acids within hydrophobic transmembrane domains of full length leukotoxin protein, preferably from *Mannheimia haemolytica*. The modified leukotoxin proteins are useful in vaccine compositions effective against *Mannheimia haemolytica* in animals.

4 Claims, 15 Drawing Sheets

FIGURE 1A

```
ATG GGA ACT AGA CTT ACA ACC CTA TCA AAT GGG CTA AAA AAC
ACT TTA ACG GCA ACC AAA AGT GGC TTA CAT AAA GCC GGT CAA
TCA TTA ACC CAA GCC GGC TCG GTT ATT GCT TCA CCG ATT GCC
TTA TTA GTA TCT GGG ATT ACC GGT GTA ATT TCT ACG ATT CTG
CAA TAT TCT AAA CAA GCA ATG TTT GAG CAC GTT GCA AAT AAA
ATT CAT AAC AAA ATT GTA GAA TGG GAA AAA AAT AAT CAC GGT
AAG AAC TAC TTT GAA AAT GGT TAC GAT GCC CGT TAT CTT GCG
AAT TTA CAA GAT AAT ATG AAA TTC TTA CTG AAC TTA AAC AAA
GAG TTA CAG GCA GAA CGT GTC ATC GCT ATT ACT CAG CAG CAA
TGG GAT AAC AAC ATT GGT GAT TTA GCT GGT ATT AGC CGT TTA
GGT GAA AAA GTC CTT AGT GGT AAA GCC TAT GTG GAT GCG TTT
GAA GAA GGC AAA CAC ATT AAA GCC GAT AAA TTA GTA CAG TTG
GAT TCG GCA AAC GGT ATT ATT GAT GTG AGT AAT TCG GGT AAA
GCG AAA ACT CAG CAT ATC TTA TTC AGA ACG CCA TTA TTG ACG
CCG GGA ACA GAG CAT CGT GAA CGC GTA CAA ACA GGT AAA TAT
GAA TAT ATT ACC AAG CTC AAT ATT AAC CGT GTA GAT AGC TGG
AAA ATT ACA GAT GGT GCA GCA AGT TCT ACC TTT GAT TTA ACT
AAC GTT GTT CAG CGT ATT GGT ATT GAA TTA GAC AAT GCT GGA
AAT GTA ACT AAA ACC AAA GAA ACA AAA ATT ATT GCC AAA CTT
GGT GAA GGT GAT GAC AAC GTA TTT GTT GGT TCT GGT ACG ACG
GAA ATT GAT GGC GGT GAA GGT TAC GAC CGA GTT CAC TAT AGC
CGT GGA AAC TAT GGT GCT TTA ACT ATT GAT GCA ACC AAA GAG
ACC GAG CAA GGT AGT TAT ACC GTA AAT CGT TTC GTA GAA ACC
GGT AAA GCA CTA CAC GAA GTG ACT TCA ACC CAT ACC GCA TTA
GTG GGC AAC CGT GAA GAA AAA ATA GAA TAT CGT CAT AGC AAT
AAC CAG CAC CAT GCC GGT TAT TAC ACC AAA GAT ACC TTG AAA
GCT GTT GAA GAA ATT ATC GGT ACA TCA CAT AAC GAT ATC TTT
AAA GGT AGT AAG TTC AAT GAT GCC TTT AAC GGT GGT GAT GGT
GTC GAT ACT ATT GAC GGT AAC GAC GGC AAT GAC CGC TTA TTT
GGT GGT AAA GGC GAT GAT ATT CTC GAT GGT GGA AAT GGT GAT
```

FIGURE 1B

GAT TTT ATC GAT GGC GGT AAA GGC AAC GAC CTA TTA CAC GGT
GGC AAG GGC GAT GAT ATT TTC GTT CAC CGT AAA GGC GAT GGT
AAT GAT ATT ATT ACC GAT TCT GAC GGC AAT GAT AAA TTA TCA
TTC TCT GAT TCG AAC TTA AAA GAT TTA ACA TTT GAA AAA GTT
AAA CAT AAT CTT GTC ATC ACG AAT AGC AAA AAA GAG AAA GTG
ACC ATT CAA AAC TGG TTC CGA GAG GCT GAT TTT GCT AAA GAA
GTG CCT AAT TAT AAA GCA ACT AAA GAT GAG AAA ATC GAA GAA
ATC ATC GGT CAA AAT GGC GAG CGG ATC ACC TCA AAG CAA GTT
GAT GAT CTT ATC GCA AAA GGT AAC GGC AAA ATT ACC CAA GAT
GAG CTA TCA AAA GTT GTT GAT AAC TAT GAA TTG CTC AAA CAT
AGC AAA AAT GTG ACA AAC AGC TTA GAT AAG TTA ATC TCA TCT
GTA AGT GCA TTT ACC TCG TCT AAT GAT TCG AGA AAT GTA TTA
GTG GCT CCA ACT TCA ATG TTG GAT CAA AGT TTA TCT TCT CTT
CAA TTT GCT AGA GCA GCT TAA

FIGURE 2A

Met Gly Thr Arg Leu Thr Thr Leu Ser Asn Gly Leu Lys Asn
Thr Leu Thr Ala Thr Lys Ser Gly Leu His Lys Ala Gly Gln
Ser Leu Thr Gln Ala Gly Ser Val Ile Ala Ser Pro Ile Ala
Leu Leu Val Ser Gly Ile Thr Gly Val Ile Ser Thr Ile Leu
Gln Tyr Ser Lys Gln Ala Met Phe Glu His Val Ala Asn Lys
Ile His Asn Lys Ile Val Glu Trp Glu Lys Asn Asn His Gly
Lys Asn Tyr Phe Glu Asn Gly Tyr Asp Ala Arg Tyr Leu Ala
Asn Leu Gln Asp Asn Met Lys Phe Leu Leu Asn Leu Asn Lys
Glu Leu Gln Ala Glu Arg Val Ile Ala Ile Thr Gln Gln Gln
Trp Asp Asn Asn Ile Gly Asp Leu Ala Gly Ile Ser Arg Leu
Gly Glu Lys Val Leu Ser Gly Lys Ala Tyr Val Asp Ala Phe
Glu Glu Gly Lys His Ile Lys Ala Asp Lys Leu Val Gln Leu
Asp Ser Ala Asn Gly Ile Ile Asp Val Ser Asn Ser Gly Lys
Ala Lys Thr Gln His Ile Leu Phe Arg Thr Pro Leu Leu Thr
Pro Gly Thr Glu His Arg Glu Arg Val Gln Thr Gly Lys Tyr
Glu Tyr Ile Thr Lys Leu Asn Ile Asn Arg Val Asp Ser Trp
Lys Ile Thr Asp Gly Ala Ala Ser Ser Thr Phe Asp Leu Thr
Asn Val Val Gln Arg Ile Gly Ile Glu Leu Asp Asn Ala Gly
Asn Val Thr Lys Thr Lys Glu Thr Lys Ile Ile Ala Lys Leu
Gly Glu Gly Asp Asp Asn Val Phe Val Gly Ser Gly Thr Thr
Glu Ile Asp Gly Gly Glu Gly Tyr Asp Arg Val His Tyr Ser
Arg Gly Asn Tyr Gly Ala Leu Thr Ile Asp Ala Thr Lys Glu
Thr Glu Gln Gly Ser Tyr Thr Val Asn Arg Phe Val Glu Thr
Gly Lys Ala Leu His Glu Val Thr Ser Thr His Thr Ala Leu
Val Gly Asn Arg Glu Glu Lys Ile Glu Tyr Arg His Ser Asn
Asn Gln His His Ala Gly Tyr Tyr Thr Lys Asp Thr Leu Lys
Ala Val Glu Glu Ile Ile Gly Thr Ser His Asn Asp Ile Phe
Lys Gly Ser Lys Phe Asn Asp Ala Phe Asn Gly Gly Asp Gly
Val Asp Thr Ile Asp Gly Asn Asp Gly Asn Asp Arg Leu Phe
Gly Gly Lys Gly Asp Asp Ile Leu Asp Gly Gly Asn Gly Asp

FIGURE 2B

Asp Phe Ile Asp Gly Gly Lys Gly Asn Asp Leu Leu His Gly
Gly Lys Gly Asp Asp Ile Phe Val His Arg Lys Gly Asp Gly
Asn Asp Ile Ile Thr Asp Ser Asp Gly Asn Asp Lys Leu Ser
Phe Ser Asp Ser Asn Leu Lys Asp Leu Thr Phe Glu Lys Val
Lys His Asn Leu Val Ile Thr Asn Ser Lys Lys Glu Lys Val
Thr Ile Gln Asn Trp Phe Arg Glu Ala Asp Phe Ala Lys Glu
Val Pro Asn Tyr Lys Ala Thr Lys Asp Glu Lys Ile Glu Glu
Ile Ile Gly Gln Asn Gly Glu Arg Ile Thr Ser Lys Gln Val
Asp Asp Leu Ile Ala Lys Gly Asn Gly Lys Ile Thr Gln Asp
Glu Leu Ser Lys Val Val Asp Asn Tyr Glu Leu Leu Lys His
Ser Lys Asn Val Thr Asn Ser Leu Asp Lys Leu Ile Ser Ser
Val Ser Ala Phe Thr Ser Ser Asn Asp Ser Arg Asn Val Leu
Val Ala Pro Thr Ser Met Leu Asp Gln Ser Leu Ser Ser Leu
Gln Phe Ala Arg Ala Ala

Kyte-Doolittle Hydropathy

FIGURE 4

FIGURE 7
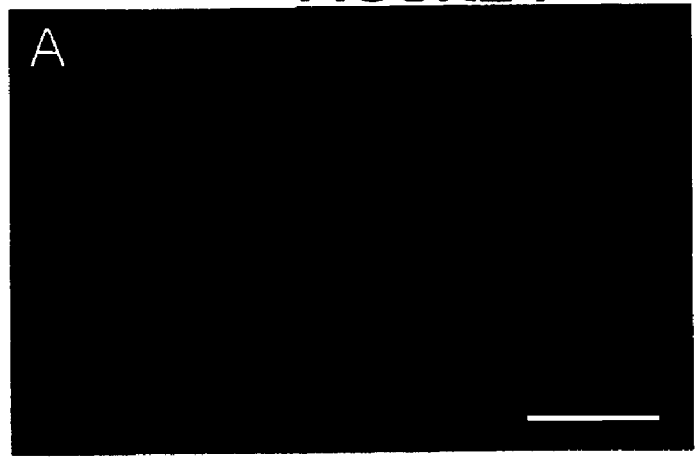
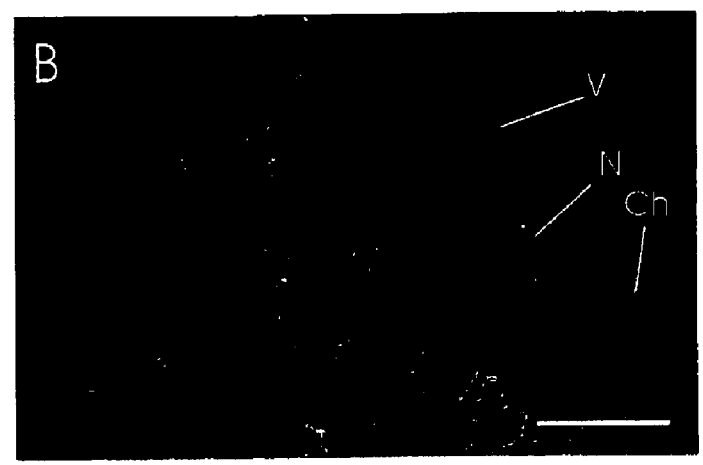
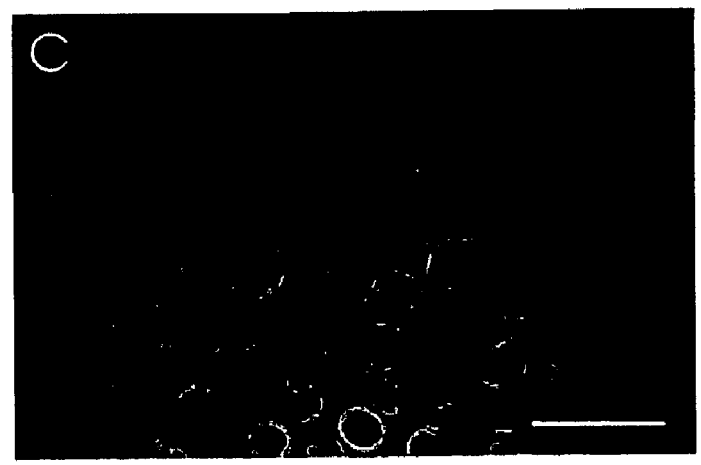

FIGURE 11

```
                AAA TTCTTACTGA ACTTAAACAA AGAGTTACAG
GCAGAACGTG TCATCGCTAT TACTCAGCAG CAATGGGATA ACAACATTGG
TGATTTAGCT GGTATTAGCC GTTTAGGTGA AAAAGTCCTT AGTGGTAAAG
CCTATGTGGA TGCGTTTGAA GAAGGCAAAC ACATTAAAGC CGATAAATTA
GTACAGTTGG ATTCGGCAAA CGGTATTATT GATGTGAGTA ATTCGGGTAA
AGCGAAAACT CAGCATATCT TATTCAGAAC GCCATTATTG ACGCCGGGAA
CAGAGCATCG TGAACGCGTA CAAACAGGTA AATATGAATA TATTACCAAG
CTCAATATTA ACCGTGTAGA TAGCTGGAAA ATTACAGATG GTGCAGCAAG
TTCTACCTTT GATTTAACTA ACGTTGTTCA GCGTATTGGT ATTGAATTAG
ACAATGCTGG AAATGTAACT AAAACCAAAG AAACAAAAAT TATTGCCAAA
CTTGGTGAAG GTGATGACAA CGTATTTGTT GGTTCTGGTA CGACGGAAAT
TGATGGCGGT GAAGGTTACG ACCGAGTTCA CTATAGCCGT GGAAACTATG
GTGCTTTAAC TATTGATGCA ACCAAGAGA CCGAGCAAGG TAGTTATACC
GTAAATCGTT TCGTAGAAAC CGGTAAAGCA CTACACGAAG TGACTTCAAC
CCATACCGCA TTAGTGGGCA ACCGTGAAGA AAAAATAGAA TATCGTCATA
GCAATAACCA GCACCATGCC GGTTATTACA CCAAAGATAC CTTGAAAGCT
GTTGAAGAAA TTATCGGTAC ATCACATAAC GATATCTTTA AAGGTAGTAA
GTTCAATGAT GCCTTTAACG GTGGTGATGG TGTCGATACT ATTGACGGTA
ACGACGGCAA TGACCGCTTA TTTGGTGGTA AAGGCGATGA TATTCTCGAT
GGTGGAAATG GTGATGATTT TATCGATGGC GGTAAAGGCA ACGACCTATT
ACACGGTGGC AAGGGCGATG ATATTTTCGT TCACCGTAAA GGCGATGGTA
ATGATATTAT TACCGATTCT GACGGCAATG ATAAATTATC ATTCTCTGAT
TCGAACTTAA AAGATTTAAC ATTTGAAAAA GTTAAACATA ATCTTGTCAT
CACGAATAGC AAAAAGAGA AAGTGACCAT TCAAAACTGG TTCCGAGAGG
CTGATTTTGC TAAAGAAGTG CCTAATTATA AAGCAACTAA AGATGAGAAA
ATCGAAGAAA TCATCGGTCA AAATGGCGAG CGGATCACCT CAAAGCAAGT
TGATGATCTT ATCGCAAAAG GTAACGGCAA AATTACCCAA GATGAGCTAT
CAAAAGTTGT TGATAACTAT GAATTG
```

FIGURE 12

Lkt50 amino acid sequence

```
FLLNLNKELQ  AERVIAITQQ  QWDNNIGDLA  GISRLGEKVL  SGKAYVDAFE
EGKHIKADKL  VQLDSANGII  DVSNSGKAKT  QHILFRTPLL  TPGTEHRERV
QTGKYEYITK  LNINRVDSWK  ITDGAASSTF  DLTNVVQRIG  IELDNAGNVT
KTKETKIIAK  LGEGDDNVFV  GSGTTEIDGG  EGYDRVHYSR  GNYGALTIDA
TKETEQGSYT  VNRFVETGKA  LHEVTSTHTA  LVGNREEKIE  YRHSNNQHHA
GYYTKDTLKA  VEEIIGTSHN  DIFKGSKFND  AFNGGDGVDT  IDGNDGNDRL
FGGKGDDILD  GGNGDDFIDG  GKGNDLLHGG  KGDDIFVHRK  GDGNDIITDS
DGNDKLSFSD  SNLKDLTFEK  VKHNLVITNS  KKEKVTIQNW  FREADFAKEV
PNYKATKDEK  IEEIIGQNGE  RITSKQVDDL  IAKGNGKITQ  DELSKVVDNY
```

FIGURE 13

```
LOCUS       LKT102          953 AA     PROT            ENTERED    01/15/97
DEFINITION  Autotranslation of LKTA
ACCESSION   -
KEYWORDS    -
SOURCE      -
ORGANISM    -
ORIGIN      A Translation of region 1-0; for LKTA
      1 MGTRLTTLSN GLKNTLTATK SGLHKAGQSL TQAGSSLKTG AKKIILYIPQ NYQYDTEQGN
     61 GLQDLVKAAE ELGIEVQREE RNNIATAQTS LGTIQTAIGL TERGIVLSAP QIDKLLQKTK
    121 AGQALGSAES IVQNANKAKT VLSGIQSILG SVLAGMDLDE ALQNNSNQHA LAKAGLELTN
    181 SLIENIANSV KTLDEFGEQI SQFGSKLQNI KGLGTLGDKL KNIGGLDKAG LGLDVISGLL
    241 SGATAALVLA DKNASTAKKV GAGFELANQV VGNITKAVSS YILAQRVAAG LSSTGPVAAL
    301 IASTVSLAIS PLAFAGIADK FNHAKSLESY AERFKKLGYD GDNLLAEYQR GTGTIDASVT
    361 AINTALAAIA GGVSAAAAGS VIASPIALLV SGITGVISTI LQYSKQAMFE HVANKIHNKI
    421 VEWEKNNHGK NYFENGYDAR YLANLQDNMK FLLNLNKELQ AERVIAITQQ QWDNNIGDLA
    481 GISRLGEKVL SGKAYVDAFE EGKHIKADKL VQLDSANGII DVSNSGKAKT QHILFRTPLL
    541 TPGTEHRERV QTGKYEYITK LNINRVDSWK ITDGAASSTF DLTNVVQRIG IELDNAGNVT
    601 KTKETKIIAK LGEGDDNVFV GSGTTEIDGG EGYDRVHYSR GNYGALTIDA TKETEQGSYT
    661 VNRFVETGKA LHEVTSTHTA LVGNREEKIE YRHSNNQHHA GYYTKDTLKA VEEIIGTSHN
    721 DIFKGSKFND AFNGGDGVDT IDGNDGNDRL FGGKGDDILD GGNGDDFIDG GKGNDLLHGG
    781 KGDDIFVHRK GDGNDIITDS DGNDKLSFSD SNLKDLTFEK VKHNLVITNS KKEKVTIQNW
    841 FREADFAKEV PNYKATKDEK IEEIIGQNGE RITSKQVDDL IAKGNGKITQ DELSKVVDNY
    901 ELLKHSKNVT NSLDKLISSV SAFTSSNDSR NVLVAPTSML DQSLSSLQFA RAA
``` under stringent hybridization conditions; (e) a nucleic acid molecule differing from any of the nucleic acids of (a) to (c) in codon sequences due to the degeneracy of the genetic code; or (f) a nucleic acid molecule that is an analog of a sequence (a) to (e).

SEQUENCE LISTING

<160> NUMBER OF SEQ ID NOS: 5

<210> SEQ ID NO 1

<211> LENGTH: 1827
<212> TYPE: DNA
<213> ORGANISM: Mannheimia haemolytica

<400> SEQUENCE: 1

```
atgggaacta gacttacaac cctatcaaat gggctaaaaa acactttaac ggcaaccaaa        60
agtggcttac ataaagccgg tcaatcatta acccaagccg gctcggttat tgcttcaccg       120
attgccttat tagtatctgg gattaccggt gtaatttcta cgattctgca atattctaaa       180
caagcaatgt ttgagcacgt tgcaaataaa attcataaca aaattgtaga atgggaaaaa       240
aataatcacg gtaagaacta ctttgaaaat ggttacgatg cccgttatct tgcgaattta       300
caagataata tgaaattctt actgaactta aacaaagagt tacaggcaga acgtgtcatc       360
gctattactc agcagcaatg ggataacaac attggtgatt tagctggtat tagccgttta       420
ggtgaaaaag tccttagtgg taaagccata gtggatgcgt ttgaagaagg caaacacatt       480
aaagccgata aattagtaca gttggattcg gcaaacggta ttattgatgt gagtaattcg       540
ggtaaagcga aaactcagca tatcttattc agaacgccat tattgacgcc gggaacagag       600
catcgtgaac gcgtacaaac aggtaaatat gaatatatta ccaagctcaa tattaaccgt       660
gtagatagct ggaaaattac agatggtgca gcaagttcta cctttgattt aactaacgtt       720
gttcagcgta ttggtattga attagacaat gctggaaatg taactaaaac caaagaaaca       780
aaaattattg ccaaacttgg tgaaggtgat gacaacgtat ttgttggttc tggtacgacg       840
gaaattgatg gcgtgaaagg ttcgaccgga gttcactata gccgtggaaa ctatggtgct       900
ttaactattg atgcaaccaa agagaccgag caaggtagtt ataccgtaaa tcgtttcgta       960
gaaccggta agcactaca cgaagtgact tcaacccata ccgcattagt gggcaaccgt      1020
gaagaaaaaa tagaatatcg tcatagcaat aaccagcacc atgccggtta ttacaccaaa      1080
gataccttga agctgttga agaaattatc ggtacatcac ataacgatat ctttaaaggt      1140
agtaagttca atgatgcctt taacggtggt gatggtgtcg atactattga cggtaacgac      1200
ggcaatgacc gcttatttgg tggtaaaggc gatgatattc tcgatggtgg aaatggtgat      1260
gattttatcg atggcggtaa aggcaacgac ctattacacg gtggcaaggg cgatgatatt      1320
ttcgttcacc gtaaaggcga tggtaatgat attattaccg attctgacgg caatgataaa      1380
ttatcattct ctgattcgaa cttaaaagat ttaacatttg aaaaagttaa acataatctt      1440
gtcatcacga atagcaaaaa agagaaagtg accattcaaa actggttccg agaggctgat      1500
tttgctaaag aagtgcctaa ttataaagca actaaagatg agaaaatcga agaaatcatc      1560
ggtcaaaatg gcgagcggat cacctcaaag caagttgatg atcttatcgc aaaaggtaac      1620
ggcaaaatta cccaagatga gctatcaaaa gttgttgata actatgaatt gctcaaacat      1680
agcaaaaatg tgacaaacag cttagataag ttaatctcat ctgtaagtgc atttacctcg      1740
tctaatgatt cgagaaatgt attagtggct ccaacttcaa tgttggatca aagtttatct      1800
tctcttcaat ttgctagagc agcttaa                                          1827
```

<210> SEQ ID NO 2
<211> LENGTH: 608
<212> TYPE: PRT
<213> ORGANISM: Mannheimia haemolytica

<400> SEQUENCE: 2

```
Met Gly Thr Arg Leu Thr Thr Leu Ser Asn Gly Leu Lys Asn Thr Leu
 1               5                  10                  15
```

-continued

```
Thr Ala Thr Lys Ser Gly Leu His Lys Ala Gly Gln Ser Leu Thr Gln
         20                  25                  30

Ala Gly Ser Val Ile Ala Ser Pro Ile Ala Leu Leu Val Ser Gly Ile
         35                  40                  45

Thr Gly Val Ile Ser Thr Ile Leu Gln Tyr Ser Lys Gln Ala Met Phe
 50                  55                  60

Glu His Val Ala Asn Lys Ile His Asn Lys Ile Val Glu Trp Glu Lys
 65                  70                  75                  80

Asn Asn His Gly Lys Asn Tyr Phe Glu Asn Gly Tyr Asp Ala Arg Tyr
                 85                  90                  95

Leu Ala Asn Leu Gln Asp Asn Met Lys Phe Leu Leu Asn Leu Asn Lys
            100                 105                 110

Glu Leu Gln Ala Glu Arg Val Ile Ala Ile Thr Gln Gln Gln Trp Asp
        115                 120                 125

Asn Asn Ile Gly Asp Leu Ala Gly Ile Ser Arg Leu Gly Glu Lys Val
130                 135                 140

Leu Ser Gly Lys Ala Tyr Val Asp Ala Phe Glu Glu Gly Lys His Ile
145                 150                 155                 160

Lys Ala Asp Lys Leu Val Gln Leu Asp Ser Ala Asn Gly Ile Ile Asp
                165                 170                 175

Val Ser Asn Ser Gly Lys Ala Lys Thr Gln His Ile Leu Phe Arg Thr
            180                 185                 190

Pro Leu Leu Thr Pro Gly Thr Glu His Arg Glu Arg Val Gln Thr Gly
        195                 200                 205

Lys Tyr Glu Tyr Ile Thr Lys Leu Asn Ile Asn Arg Val Asp Ser Trp
    210                 215                 220

Lys Ile Thr Asp Gly Ala Ala Ser Ser Thr Phe Asp Leu Thr Asn Val
225                 230                 235                 240

Val Gln Arg Ile Gly Ile Glu Leu Asp Asn Ala Gly Asn Val Thr Lys
                245                 250                 255

Thr Lys Glu Thr Lys Ile Ile Ala Lys Leu Gly Glu Gly Asp Asp Asn
            260                 265                 270

Val Phe Val Gly Ser Gly Thr Thr Glu Ile Asp Gly Gly Glu Gly Tyr
        275                 280                 285

Asp Arg Val His Tyr Ser Arg Gly Asn Tyr Gly Ala Leu Thr Ile Asp
    290                 295                 300

Ala Thr Lys Glu Thr Glu Gln Gly Ser Tyr Thr Val Asn Arg Phe Val
305                 310                 315                 320

Glu Thr Gly Lys Ala Leu His Glu Val Thr Ser Thr His Thr Ala Leu
                325                 330                 335

Val Gly Asn Arg Glu Glu Lys Ile Glu Tyr Arg His Ser Asn Asn Gln
            340                 345                 350

His His Ala Gly Tyr Tyr Thr Lys Asp Thr Leu Lys Ala Val Glu Glu
        355                 360                 365

Ile Ile Gly Thr Ser His Asn Asp Ile Phe Lys Gly Ser Lys Phe Asn
    370                 375                 380

Asp Ala Phe Asn Gly Gly Asp Gly Val Asp Thr Ile Asp Gly Asn Asp
385                 390                 395                 400

Gly Asn Asp Arg Leu Phe Gly Gly Lys Gly Asp Asp Ile Leu Asp Gly
                405                 410                 415

Gly Asn Gly Asp Asp Phe Ile Asp Gly Gly Lys Gly Asn Asp Leu Leu
            420                 425                 430

His Gly Gly Lys Gly Asp Asp Ile Phe Val His Arg Lys Gly Asp Gly
```

-continued

```
                435                 440                 445
Asn Asp Ile Ile Thr Asp Ser Asp Gly Asn Asp Lys Leu Ser Phe Ser
    450                 455                 460

Asp Ser Asn Leu Lys Asp Leu Thr Phe Glu Lys Val Lys His Asn Leu
465                 470                 475                 480

Val Ile Thr Asn Ser Lys Lys Glu Lys Val Thr Ile Gln Asn Trp Phe
                485                 490                 495

Arg Glu Ala Asp Phe Ala Lys Glu Val Pro Asn Tyr Lys Ala Thr Lys
            500                 505                 510

Asp Glu Lys Ile Glu Glu Ile Gly Gln Asn Gly Glu Arg Ile Thr
        515                 520                 525

Ser Lys Gln Val Asp Asp Leu Ile Ala Lys Gly Asn Gly Lys Ile Thr
    530                 535                 540

Gln Asp Glu Leu Ser Lys Val Val Asp Asn Tyr Glu Leu Leu Lys His
545                 550                 555                 560

Ser Lys Asn Val Thr Asn Ser Leu Asp Lys Leu Ile Ser Ser Val Ser
                565                 570                 575

Ala Phe Thr Ser Ser Asn Asp Ser Arg Asn Val Leu Val Ala Pro Thr
            580                 585                 590

Ser Met Leu Asp Gln Ser Leu Ser Ser Leu Gln Phe Ala Arg Ala Ala
        595                 600                 605

<210> SEQ ID NO 3
<211> LENGTH: 1359
<212> TYPE: DNA
<213> ORGANISM: Mannheimia haemolytica

<400> SEQUENCE: 3
aaattcttac tgaacttaaa caaagagtta caggcagaac gtgtcatcgc tattactcag      60
cagcaatggg ataacaacat tggtgattta gctggtatta gccgtttagg tgaaaaagtc     120
cttagtggta agcctatgt ggatgcgttt gaagaaggca acacattaa agccgataaa       180 ttagtacagt tggattcggc aaacggtatt attgatgtga gtaattcggg taaagcgaaa     240
actcagcata tcttattcag aacgccatta ttgacgccgg aacagagca tcgtgaacgc     300 gtacaaacag gtaaatatga atatattacc aagctcaata ttaaccgtgt agatagctgg     360
aaaattacag atggtgcagc aagttctacc tttgatttaa ctaacgttgt tcagcgtatt     420
ggtattgaat tagacaatgc tggaaatgta actaaaacca agaaacaaa aattattgcc     480 aaacttggtg aaggtgatga caacgtattt gttggttctg gtacgacgga aattgatggc     540
ggtgaaggtt acgaccgagt tcactatagc cgtggaaact atggtgcttt aactattgat     600
gcaaccaaag agaccgagca aggtagttat accgtaaatc gtttcgtaga accggtaaa      660 gcactacacg aagtgacttc aacccatacc gcattagtgg gcaaccgtga agaaaaaata     720
gaatatcgtc atagcaataa ccagcaccat gccggttatt acaccaaaga taccttgaaa     780
gctgttgaag aaattatcgg tacatcacat aacgatatct ttaaaggtag taagttcaat     840
gatgccttta acggtggtga tggtgtcgat actattgacg gtaacgacgg caatgaccgc     900
ttatttggtg gtaaaggcga tgatattctc gatggtggaa atggtgatga ttttatcgat     960
ggcggtaaag gcaacgacct attacacggt ggcaagggcg atgatatttt cgttcaccgt    1020
aaaggcgatg gtaatgatat tattaccgat tctgacggca atgataaatt atcattctct    1080
gattcgaact aaaagatttt aacatttgaa aaagttaaac ataatcttgt catcacgaat    1140
agcaaaaaag agaaagtgac cattcaaaac tggttccgag aggctgattt tgctaaagaa    1200
```

```
gtgcctaatt ataaagcaac taaagatgag aaaatcgaag aaatcatcgg tcaaaatggc   1260
gagcggatca cctcaaagca agttgatgat cttatcgcaa aaggtaacgg caaaattacc   1320
caagatgagc tatcaaaagt tgttgataac tatgaattg                         1359
```

<210> SEQ ID NO 4
<211> LENGTH: 450
<212> TYPE: PRT
<213> ORGANISM: Mannheimia haemolytica

<400> SEQUENCE: 4

```
Phe Leu Leu Asn Leu Asn Lys Glu Leu Gln Ala Glu Arg Val Ile Ala
1               5                   10                  15

Ile Thr Gln Gln Gln Trp Asp Asn Asn Ile Gly Asp Leu Ala Gly Ile
            20                  25                  30

Ser Arg Leu Gly Glu Lys Val Leu Ser Gly Lys Ala Tyr Val Asp Ala
        35                  40                  45

Phe Glu Glu Gly Lys His Ile Lys Ala Asp Lys Leu Val Gln Leu Asp
    50                  55                  60

Ser Ala Asn Gly Ile Ile Asp Val Ser Asn Ser Gly Lys Ala Lys Thr
65                  70                  75                  80

Gln His Ile Leu Phe Arg Thr Pro Leu Leu Thr Pro Gly Thr Glu His
                85                  90                  95

Arg Glu Arg Val Gln Thr Gly Lys Tyr Glu Tyr Ile Thr Lys Leu Asn
            100                 105                 110

Ile Asn Arg Val Asp Ser Trp Lys Ile Thr Asp Gly Ala Ala Ser Ser
        115                 120                 125

Thr Phe Asp Leu Thr Asn Val Val Gln Arg Ile Gly Ile Glu Leu Asp
    130                 135                 140

Asn Ala Gly Asn Val Thr Lys Thr Lys Glu Thr Lys Ile Ile Ala Lys
145                 150                 155                 160

Leu Gly Glu Gly Asp Asp Asn Val Phe Val Gly Ser Gly Thr Thr Glu
                165                 170                 175

Ile Asp Gly Gly Glu Gly Tyr Asp Arg Val His Tyr Ser Arg Gly Asn
            180                 185                 190

Tyr Gly Ala Leu Thr Ile Asp Ala Thr Lys Glu Thr Glu Gln Gly Ser
        195                 200                 205

Tyr Thr Val Asn Arg Phe Val Glu Thr Gly Lys Ala Leu His Glu Val
    210                 215                 220

Thr Ser Thr His Thr Ala Leu Val Gly Asn Arg Glu Glu Lys Ile Glu
225                 230                 235                 240

Tyr Arg His Ser Asn Asn Gln His His Ala Gly Tyr Tyr Thr Lys Asp
                245                 250                 255

Thr Leu Lys Ala Val Glu Glu Ile Ile Gly Thr Ser His Asn Asp Ile
            260                 265                 270

Phe Lys Gly Ser Lys Phe Asn Asp Ala Phe Asn Gly Gly Asp Gly Val
        275                 280                 285

Asp Thr Ile Asp Gly Asn Asp Gly Asn Asp Arg Leu Phe Gly Gly Lys
    290                 295                 300

Gly Asp Asp Ile Leu Asp Gly Gly Asn Gly Asp Asp Phe Ile Asp Gly
305                 310                 315                 320

Gly Lys Gly Asn Asp Leu Leu His Gly Gly Lys Gly Asp Asp Ile Phe
                325                 330                 335

Val His Arg Lys Gly Asp Gly Asn Asp Ile Ile Thr Asp Ser Asp Gly
```

```
                340                 345                 350
Asn Asp Lys Leu Ser Phe Ser Asp Ser Asn Leu Lys Asp Leu Thr Phe
            355                 360                 365

Glu Lys Val Lys His Asn Leu Val Ile Thr Asn Ser Lys Lys Glu Lys
        370                 375                 380

Val Thr Ile Gln Asn Trp Phe Arg Glu Ala Asp Phe Ala Lys Glu Val
385                 390                 395                 400

Pro Asn Tyr Lys Ala Thr Lys Asp Glu Lys Ile Glu Glu Ile Ile Gly
                405                 410                 415

Gln Asn Gly Glu Arg Ile Thr Ser Lys Gln Val Asp Asp Leu Ile Ala
            420                 425                 430

Lys Gly Asn Gly Lys Ile Thr Gln Asp Glu Leu Ser Lys Val Val Asp
        435                 440                 445

Asn Tyr
    450

<210> SEQ ID NO 5
<211> LENGTH: 953
<212> TYPE: PRT
<213> ORGANISM: Mannheimia haemolytica

<400> SEQUENCE: 5

Met Gly Thr Arg Leu Thr Thr Leu Ser Asn Gly Leu Lys Asn Thr Leu
1               5                   10                  15

Thr Ala Thr Lys Ser Gly Leu His Lys Ala Gly Gln Ser Leu Thr Gln
            20                  25                  30

Ala Gly Ser Ser Leu Lys Thr Gly Ala Lys Lys Ile Ile Leu Tyr Ile
        35                  40                  45

Pro Gln Asn Tyr Gln Tyr Asp Thr Glu Gln Gly Asn Gly Leu Gln Asp
    50                  55                  60

Leu Val Lys Ala Ala Glu Glu Leu Gly Ile Glu Val Gln Arg Glu Glu
65                  70                  75                  80

Arg Asn Asn Ile Ala Thr Ala Gln Thr Ser Leu Gly Thr Ile Gln Thr
                85                  90                  95

Ala Ile Gly Leu Thr Glu Arg Gly Ile Val Leu Ser Ala Pro Gln Ile
            100                 105                 110

Asp Lys Leu Leu Gln Lys Thr Lys Ala Gly Gln Ala Leu Gly Ser Ala
        115                 120                 125

Glu Ser Ile Val Gln Asn Ala Asn Lys Ala Lys Thr Val Leu Ser Gly
    130                 135                 140

Ile Gln Ser Ile Leu Gly Ser Val Leu Ala Gly Met Asp Leu Asp Glu
145                 150                 155                 160

Ala Leu Gln Asn Asn Ser Asn Gln His Ala Leu Ala Lys Ala Gly Leu
                165                 170                 175

Glu Leu Thr Asn Ser Leu Ile Glu Asn Ile Ala Asn Ser Val Lys Thr
            180                 185                 190

Leu Asp Glu Phe Gly Glu Gln Ile Ser Gln Phe Gly Ser Lys Leu Gln
        195                 200                 205

Asn Ile Lys Gly Leu Gly Thr Leu Gly Asp Lys Leu Lys Asn Ile Gly
    210                 215                 220

Gly Leu Asp Lys Ala Gly Leu Gly Leu Asp Val Ile Ser Gly Leu Leu
225                 230                 235                 240

Ser Gly Ala Thr Ala Ala Leu Val Leu Ala Asp Lys Asn Ala Ser Thr
                245                 250                 255
```

-continued

Ala Lys Lys Val Gly Ala Gly Phe Glu Leu Ala Asn Gln Val Val Gly
        260                 265                 270

Asn Ile Thr Lys Ala Val Ser Ser Tyr Ile Leu Ala Gln Arg Val Ala
        275                 280                 285

Ala Gly Leu Ser Ser Thr Gly Pro Val Ala Ala Leu Ile Ala Ser Thr
        290                 295                 300

Val Ser Leu Ala Ile Ser Pro Leu Ala Phe Ala Gly Ile Ala Asp Lys
305                 310                 315                 320

Phe Asn His Ala Lys Ser Leu Glu Ser Tyr Ala Glu Arg Phe Lys Lys
                325                 330                 335

Leu Gly Tyr Asp Gly Asp Asn Leu Leu Ala Glu Tyr Gln Arg Gly Thr
                340                 345                 350

Gly Thr Ile Asp Ala Ser Val Thr Ala Ile Asn Thr Ala Leu Ala Ala
                355                 360                 365

Ile Ala Gly Gly Val Ser Ala Ala Ala Gly Ser Val Ile Ala Ser
        370                 375                 380

Pro Ile Ala Leu Leu Val Ser Gly Ile Thr Gly Val Ile Ser Thr Ile
385                 390                 395                 400

Leu Gln Tyr Ser Lys Gln Ala Met Phe Glu His Val Ala Asn Lys Ile
                405                 410                 415

His Asn Lys Ile Val Glu Trp Glu Lys Asn Asn His Gly Lys Asn Tyr
                420                 425                 430

Phe Glu Asn Gly Tyr Asp Ala Arg Tyr Leu Ala Asn Leu Gln Asp Asn
        435                 440                 445

Met Lys Phe Leu Leu Asn Leu Asn Lys Glu Leu Gln Ala Glu Arg Val
        450                 455                 460

Ile Ala Ile Thr Gln Gln Gln Trp Asp Asn Ile Gly Asp Leu Ala
465                 470                 475                 480

Gly Ile Ser Arg Leu Gly Glu Lys Val Leu Ser Gly Lys Ala Tyr Val
                485                 490                 495

Asp Ala Phe Glu Glu Gly Lys His Ile Lys Ala Asp Lys Leu Val Gln
                500                 505                 510

Leu Asp Ser Ala Asn Gly Ile Ile Asp Val Ser Asn Ser Gly Lys Ala
        515                 520                 525

Lys Thr Gln His Ile Leu Phe Arg Thr Pro Leu Leu Thr Pro Gly Thr
        530                 535                 540

Glu His Arg Glu Arg Val Gln Thr Gly Lys Tyr Glu Tyr Ile Thr Lys
545                 550                 555                 560

Leu Asn Ile Asn Arg Val Asp Ser Trp Lys Ile Thr Asp Gly Ala Ala
                565                 570                 575

Ser Ser Thr Phe Asp Leu Thr Asn Val Val Gln Arg Ile Gly Ile Glu
        580                 585                 590

Leu Asp Asn Ala Gly Asn Val Thr Lys Thr Lys Glu Thr Lys Ile Ile
        595                 600                 605

Ala Lys Leu Gly Glu Gly Asp Asp Asn Val Phe Val Gly Ser Gly Thr
        610                 615                 620

Thr Glu Ile Asp Gly Gly Glu Gly Tyr Asp Arg Val His Tyr Ser Arg
625                 630                 635                 640

Gly Asn Tyr Gly Ala Leu Thr Ile Asp Ala Thr Lys Glu Thr Glu Gln
                645                 650                 655

Gly Ser Tyr Thr Val Asn Arg Phe Val Glu Thr Gly Lys Ala Leu His
                660                 665                 670

Glu Val Thr Ser Thr His Thr Ala Leu Val Gly Asn Arg Glu Glu Lys

-continued

```
                675              680              685
Ile Glu Tyr Arg His Ser Asn Asn Gln His His Ala Gly Tyr Tyr Thr
        690              695              700

Lys Asp Thr Leu Lys Ala Val Glu Glu Ile Ile Gly Thr Ser His Asn
705              710              715              720

Asp Ile Phe Lys Gly Ser Lys Phe Asn Asp Ala Phe Asn Gly Gly Asp
                725              730              735

Gly Val Asp Thr Ile Asp Gly Asn Asp Gly Asn Asp Arg Leu Phe Gly
            740              745              750

Gly Lys Gly Asp Asp Ile Leu Asp Gly Gly Asn Gly Asp Asp Phe Ile
        755              760              765

Asp Gly Gly Lys Gly Asn Asp Leu Leu His Gly Gly Lys Gly Asp Asp
770              775              780

Ile Phe Val His Arg Lys Gly Asp Gly Asn Asp Ile Ile Thr Asp Ser
785              790              795              800

Asp Gly Asn Asp Lys Leu Ser Phe Ser Asp Ser Asn Leu Lys Asp Leu
            805              810              815

Thr Phe Glu Lys Val Lys His Asn Leu Val Ile Thr Asn Ser Lys Lys
            820              825              830

Glu Lys Val Thr Ile Gln Asn Trp Phe Arg Glu Ala Asp Phe Ala Lys
        835              840              845

Glu Val Pro Asn Tyr Lys Ala Thr Lys Asp Glu Lys Ile Glu Glu Ile
    850              855              860

Ile Gly Gln Asn Gly Glu Arg Ile Thr Ser Lys Gln Val Asp Asp Leu
865              870              875              880

Ile Ala Lys Gly Asn Gly Lys Ile Thr Gln Asp Glu Leu Ser Lys Val
            885              890              895

Val Asp Asn Tyr Glu Leu Leu Lys His Ser Lys Asn Val Thr Asn Ser
            900              905              910

Leu Asp Lys Leu Ile Ser Ser Val Ser Ala Phe Thr Ser Ser Asn Asp
        915              920              925

Ser Arg Asn Val Leu Val Ala Pro Thr Ser Met Leu Asp Gln Ser Leu
    930              935              940

Ser Ser Leu Gln Phe Ala Arg Ala Ala
945              950
```

MODIFIED LEUKOTOXIN PROTEIN

This application is a divisional of U.S. patent application Ser. No. 10/148,884, filed Oct. 22, 2002 (now allowed), which is a national phase entry application of international application serial no. PCT/CA00/01498, filed Dec. 15, 2000 (now expired), which claims priority from U.S. provisional patent application No. 60/172,148, filed Dec. 17, 1999 (now expired).

FIELD OF THE INVENTION

This invention relates to the construction and expression of a modified leukotoxin gene and to the use of the modified leukotoxin as a vaccine.

BACKGROUND OF THE INVENTION

Bovine pneumonic pasteurellosis, also known as shipping fever, is a major cause of sickness and death in the feedlot cattle industry (Martin, S. W. et al. Can. J. Comp. Med. 1980, 44:1-10; Yates, W. D. G. Can. J. Comp. Med. 1982, 46:225-263). The principal microorganism associated with this disease is *Mannheimia* (*Pasteurella*) *haemolytica* A1. It has been shown that *M. haemolytica* produces a heat labile cytotoxin which is specific against ruminant leukocytes (Kaehler, K. L. et al. Am. J. Vet. Res. 1980, 41:1690-1693; Shewen, P. E. et al. Infect. Immun. 1982, 35:91-94). This leukotoxin has been implicated as a major virulence factor in the pathogenesis of *M. haemolytica*. Its mode of action has been shown to be the impairment of the primary lung defense mechanism (inactivation of alveolar macrophages) and the induction of inflammation as a consequence of leukocyte lysis.

In the past, vaccination against *M. haemolytica* infection has been attempted using both live and heat-killed bacteria of various serotypes. It has been demonstrated that vaccination with heat-killed bacteria may actually enhance the development of pneumonia after challenge exposure (Sanford, S. E. Mod. Vet. Prac. 1984, 65:265-268). Immunization with live *M. haemolytica* vaccines have generally been unsuccessful because of low antigenicity of *M. haemolytica* cells and rapid inactivation by the healthy animal (Henry, C. W. Vet. Med. 1984, 1200-1206). The cytotoxic supernatant from *M. haemolytica* has also been used as a vaccine. This preparation contains numerous soluble antigens from the bacterium, some of which may be important in protection. Development of vaccines from the crude cytotoxic supernate requires the purification and characterization of these antigens which is difficult and costly.

Advances in molecular biology have allowed the characterization, isolation and expression of the particular genes which code for specific bacterial antigens using various recombinant DNA techniques. In fact, the gene, lktA, that codes for the full length leukotoxin (Lkt-102) of *M. haemolytica* has been well characterized (Lo, R. Y. C. et al. Infect. Immun., 1987, 55:1987-1996, Lo, R. Y. C. et al. U.S. Pat. No. 5,055,400). However, when the full length recombinant leukotoxin is produced in *E. coli*, it is very unstable and quickly degrades. The yield and recovery of the 102 kDa rLkt is therefore very poor, rendering this method of obtaining recombinant leukotoxin for use as a vaccine, costly and inefficient.

There remains a need for a highly stable derivative of the recombinant leukotoxin that retains the antigenic and immunogenic properties of the full length protein.

SUMMARY OF THE INVENTION

The present inventors have prepared modified leukotoxin proteins wherein the hydrophobic transmembrane domains of the leukotoxin protein of *Mannheimia haemolytica* have been removed. The modified leukotoxin protein is incapable of inserting into target cells rendering it devoid of toxic activity. Consequently, the modified protein is extremely useful in the preparation of vaccines. Further, the inventors have shown that the modified leukotoxin protein is highly stable and when prepared by recombinant means is produced at several fold higher levels than full length leukotoxin. In addition, the modified leukotoxin protein retains its ability to stimulate an immune response.

Accordingly, the present invention provides an isolated nucleic acid molecule comprising a nucleotide sequence that encodes a modified leukotoxin protein, wherein the modification comprises the removal of nucleic acid sequences encoding amino acids within a hydrophobic transmembrane domain of a full length leukotoxin.

In a preferred embodiment, a purified and isolated nucleic acid molecule is provided which encodes (a) a modified leukotoxin protein as shown in FIGS. 2A and 2B or (b) a modified leukotoxin protein as shown in FIG. 12.

In one embodiment, the purified and isolated nucleic acid molecule comprises: (a) a nucleic acid sequence as shown in FIGS. 1A and 1B, wherein T can also be U; (b) nucleic acid sequences complementary to (a); (c) nucleic acid sequences which have substantial sequence homology to (a) or (b); (d) a fragment of (a) to (c) that is at least 15 bases, preferably 20 to 30 bases, and which will hybridize to (a) to (c) under stringent hybridization conditions; (e) a nucleic acid molecule differing from any of the nucleic acids of (a) to (c) in codon sequences due to the degeneracy of the genetic code; or (f) a nucleic acid molecule that is an analog of a sequence (a) to (e).

In another embodiment, the purified and isolated nucleic acid molecule comprises: (a) a nucleic acid sequence as shown in FIG. 11, wherein T can also be U; (b) nucleic acid sequences complementary to (a); (c) nucleic acid sequences which have substantial sequence homology to (a) or (b); (d) a fragment of (a) to (c) that is at least 15 bases, preferably 20 to 30 bases, and which will hybridize to (a) to (c) under stringent hybridization conditions; (e) a nucleic acid molecule differing from any of the nucleic acids of (a) to (c) in codon sequences due to the degeneracy of the genetic code; or (f) a nucleic acid molecule that is an analog of a sequence (a) to (e).

In another aspect, the present invention includes an expression cassette comprising (a) a nucleic acid sequence encoding a modified leukotoxin, wherein the modification comprises the removal of nucleic acid sequences encoding amino acids within a hydrophobic transmembrane domain of the full length leukotoxin protein; and (b) control sequences that are operably linked to the nucleic acid sequence whereby the nucleic acid sequence can be transcribed and translated in a host cell.

In a further aspect, the present invention provides a plasmid comprising a nucleic acid sequence encoding a modified leukotoxin protein, wherein the modification comprises the removal of nucleic acid sequences encoding amino acids within a hydrophobic transmembrane domain of the full length leukotoxin protein.

The present invention further involves host cells and microorganisms transformed with a construct or plasmid of the invention.

There is also provided a method for producing a recombinant modified leukotoxin protein, wherein the modification comprises the removal of amino acids within a hydrophobic transmembrane domain of the full length leukotoxin protein, comprising the steps of:

(a) transforming a host cell with a nucleotide sequence of the invention;

(b) culturing the transformed host cell under suitable conditions to produce the modified leukotoxin; and (c) isolating the modified leukotoxin protein.

The invention also includes a method for the production of a modified leukotoxin in a host cell comprising:

a) introducing into the host cell a chimeric nucleic acid sequence molecule comprising in the 5' to 3' direction of transcription:

1) a first nucleic acid sequence capable of regulating transcription in said host cell operatively linked to;
2) a second nucleic acid sequence encoding a modified leukotoxin protein operatively linked to;
3) a third nucleic acid sequence capable of terminating transcription in said host cell; and b) culturing said host cell under suitable conditions to allow said cell to express the modified leukotoxin protein.

In one embodiment, the host cell is a bacteria. In another embodiment, the host cell is a plant.

Further, the present invention provides a method for producing a recombinant modified leukotoxin protein as described above, wherein the modified leukotoxin protein has the amino acid sequence shown in FIGS. 2A and 2B or as shown in FIG. 12, or a homolog, analog, derivative or fragment thereof.

The present invention also provides a purified and isolated polypeptide having an amino acid sequence of a modified leukotoxin protein, preferably having the amino acid sequence shown in FIGS. 2A and 2B or as shown in FIG. 12, or a homolog, analog, derivative or fragment thereof.

The present invention extends to cover polyclonal and monoclonal antibodies raised to a modified leukotoxin, wherein the modification comprises the removal of amino acids within a hydrophobic transmembrane domain of a full length leukotoxin protein, or a modified leukotoxin that is a homolog, analog, derivative or fragment thereof.

The present invention is also directed to a vaccine composition comprising a pharmaceutically acceptable carrier and a modified leukotoxin, wherein the modification comprises the removal of amino acids within a hydrophobic transmembrane domain of the full length leukotoxin protein, or a homolog, analog, derivative or fragment thereof.

The present invention also involves a vaccine composition comprising a pharmaceutically acceptable carrier and a nucleic acid sequence encoding a modified leukotoxin protein, wherein the modification comprises the removal of sequences encoding amino acids within a hydrophobic transmembrane domain of the full length leukotoxin protein, or a nucleic acid sequence encoding a homolog, analog, derivative or fragment of the modified leukotoxin protein.

In still another aspect of the present invention, there are provided methods for preventing or treating an infection associated with a leukotoxin such as respiratory disease in an animal comprising administering an effective amount of a modified leukotoxin gene or protein of the invention to an animal in need thereof.

In still another aspect of the present invention, there are provided methods for preventing or treating a *Mannheimia* infection, preferably a *Mannheimia haemolytica* infection in an animal comprising administering an effective amount of a modified leukotoxin gene or protein of the invention to an animal in need thereof.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The features of the present invention will become more apparent from the following description in which reference is made to the appended drawings in which:

FIGS. 1A and 1B (SEQ.ID.NO.:1) shows the nucleic acid sequence coding for a modified leukotoxin (lkt66) of the invention.

FIGS. 2A and 2B (SEQ.ID.NO.:2) shows the shows the amino acid sequence for a modified leukotoxin (lkt66) of the invention.

Figure 4:
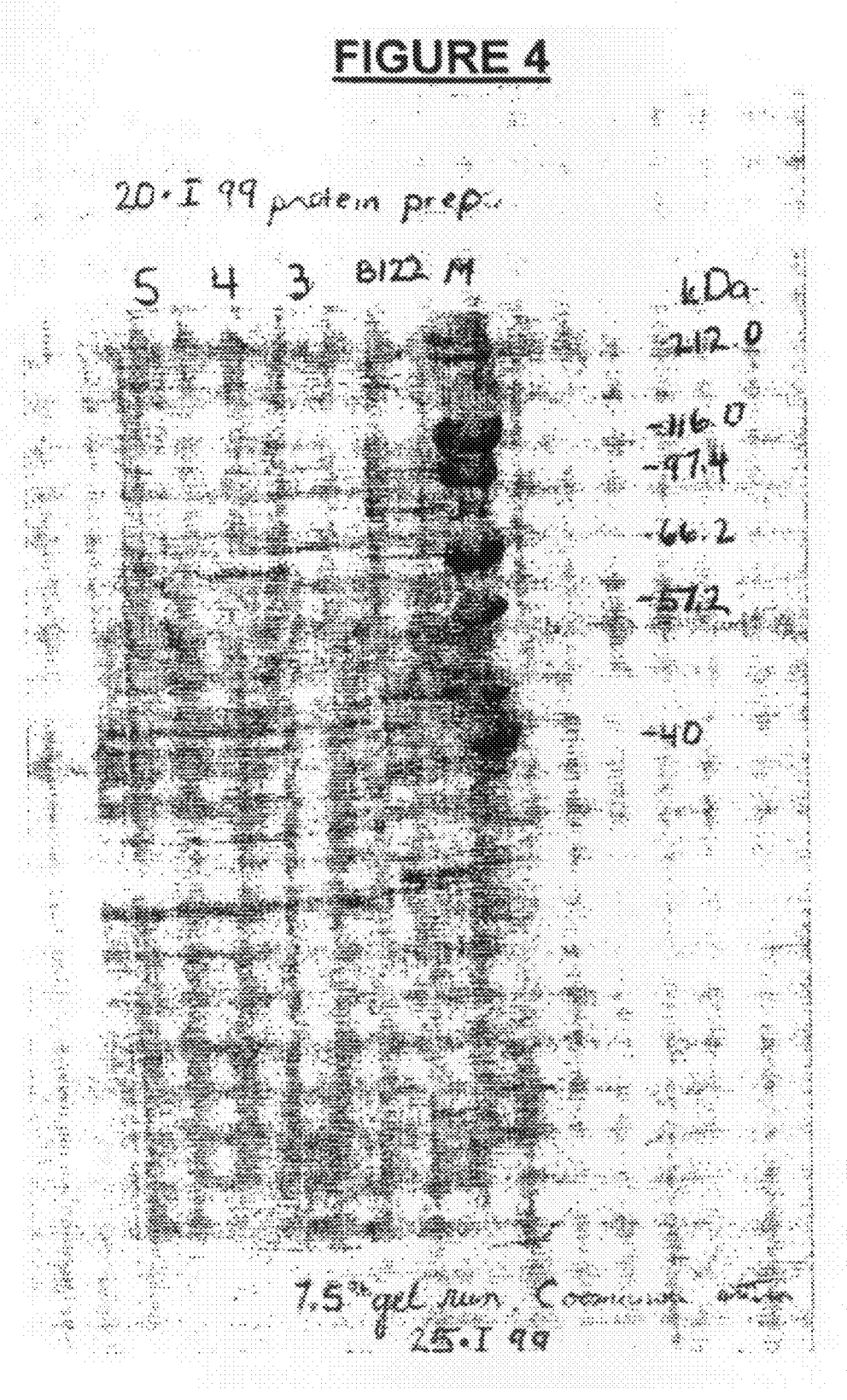

FIG. 4 is a Coomassie stained SDS-PAGE where lane #3 is from the expression of the full length Lkt-102 in *E. coli*, lane #4 is from the expression of the modified Lkt-66 in *E. coli* and lane #5 is a negative sample where no Lkt protein was present.

FIG. 7 shows the laser confocal microscopy of transgenic white clover expressing Lkt50-mGFP5. A section of clover leaf was mounted in water and observed by confocal microscopy. Images from two channels (red for chlorophyll fluorescence and green for mGFP5 fluorescence) were merged to produce the micrographs shown. Leaves from untransformed clover (A) do not exhibit the green fluorescence which is present in transgenic clover expressing Lkt50-mGFP5 (B). The pattern of green fluorescence is consistent with an ER localization. The bar indicates 100 µm. Vacuoles (V), nuclei (N), and chloroplasts (Ch) are indicated in panel 8.

FIG. 11 (SEQ.ID.NO.:3) shows the nucleic acid sequence coding for a modified leukotoxin (lkt50) of the invention.

FIG. 12 (SEQ.ID.NO.:4) shows the shows the amino acid sequence for a modified leukotoxin (lkt50) of the invention.

FIG. 13 (SEQ.ID.NO.:5) shows the amino acid sequence of the full length leukotoxin protein from M. haemolytica.

DETAILED DESCRIPTION OF THE INVENTION

Figure 3:
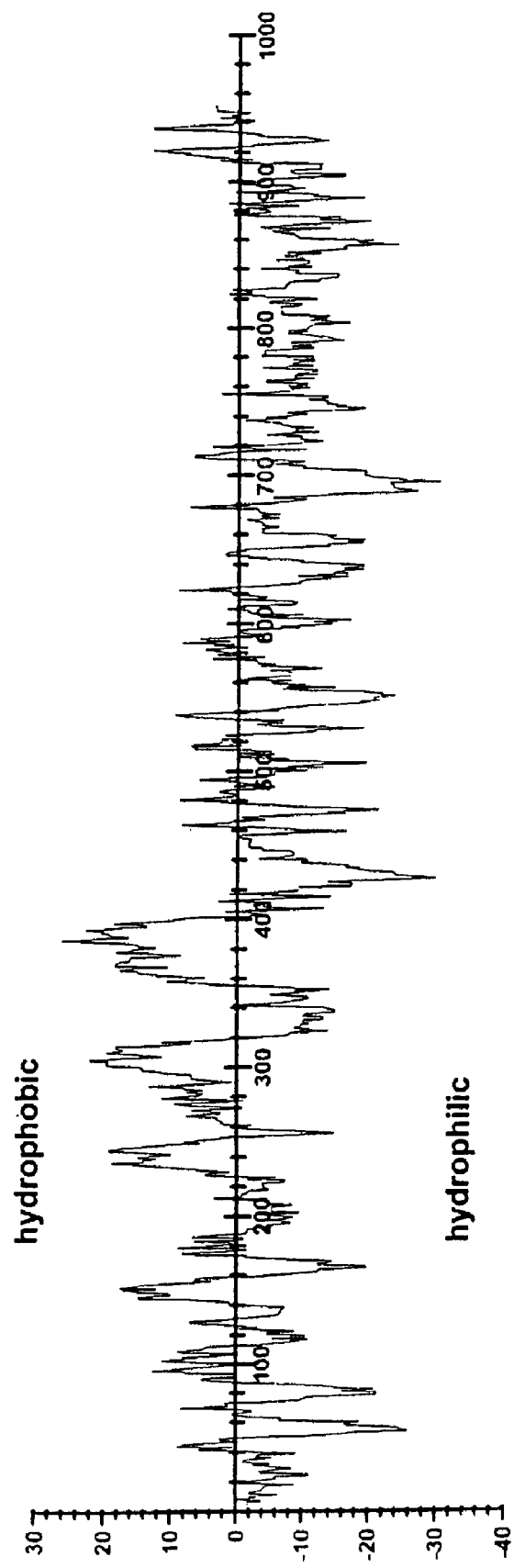
FIG. 3 is a Kyte-Doolittle hydropathy plot of the full length leukotoxin protein showing the hydrophobic (positive) and hydrophilic (negative) regions.
Figure 5:
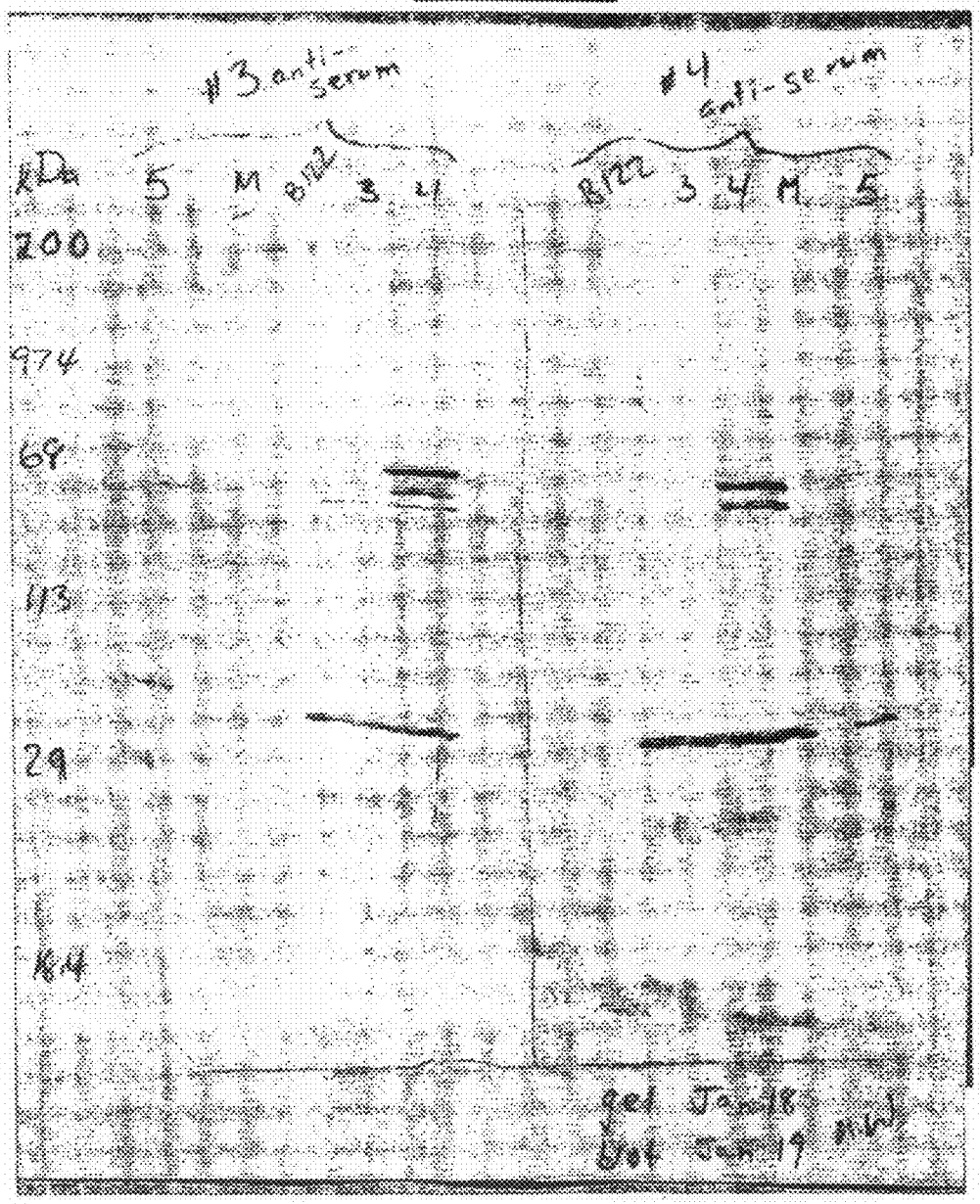
FIG. 5 is a Western immunoblot of a duplicate set of protein preparations immunostained with rabbit anti-Lkt102 (#3) and anti-Lkt66 (#4).
Figure 6:
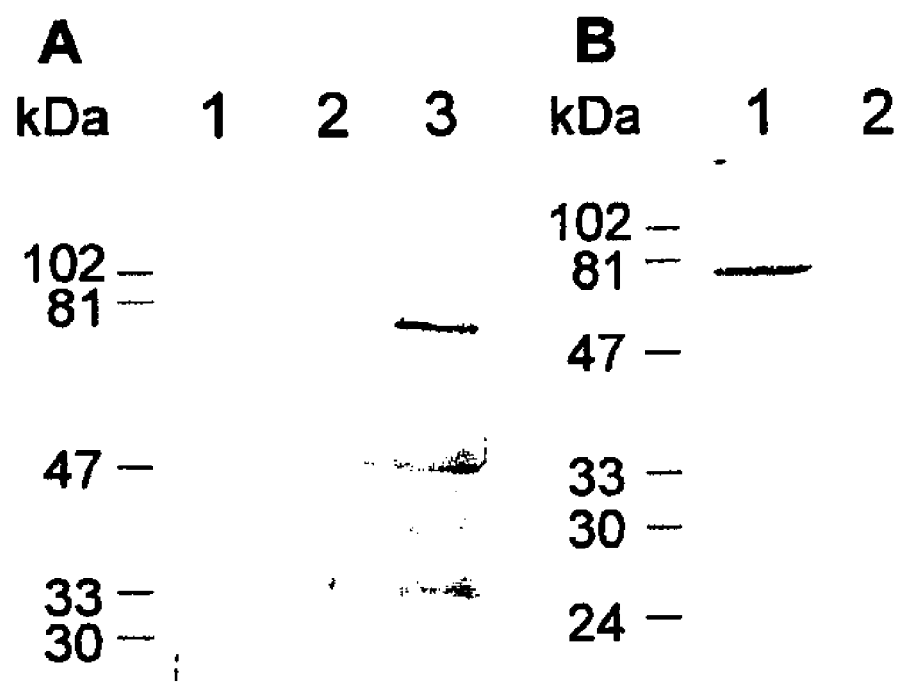
FIG. 6 shows the transient expression of chimeric genes in tobacco. (A) Protein extracted from tobacco leaves infiltrated with *Agrobacterium*, transformed with constructs containing promoterless modified green fluorescent protein mGFP5 (lane 1), 35S-mGFP5 (lane 2) or 35S-Lkt50-mGFP5 (lane 3), were blotted and probed with rabbit anti-Lkt66 antiserum. The resulting Western immunoblot is shown. A cross-reacting band was observed only in lane 3 where the presence of the Lkt50-containing fusion protein was expected. (B) The expression of Lkt50-mGFP5 (lane 1) and mGFP5-Lkt50 (lane 2) was analyzed by Western immunoblot with the rabbit anti-Lkt66 antiserum as above. *Agrobacterium* transformed with vectors containing either 35S-Lkt50-mGFP5 (lane 1) or 35S-mGFP5-Lkt50 (lane 2) was used for infiltration. Only in the case where mGFP5 was fused to the C-terminus of the *M. haemolytica* A1 Lkt50 (lane 1) was fusion protein expression detected. Migration of the molecular weight markers are indicated on the right.

The following standard abbreviations for the amino acid residues are used throughout the specification: A, Ala—alanine; C, Cys—cysteine; D, Asp—aspartic acid; E, Glu—glutamic acid; F, Phe—phenylalanine; G, Gly—glycine; H, His—histidine; I, Ile—isoleucine; K, Lys—lysine; L, Leu—leucine; M, Met—methionine; N, Asn—asparagine; P, Pro—proline; Q, Gln—glutamine; R, Arg—arginine; S, Ser—serine; T, Thr—threonine; V, Val—valine; W, Trp—tryptophan; Y, Tyr—tyrosine; and p.Y., P.Tyr—phosphotyrosine.

The practice of the present invention employs, unless otherwise indicated, conventional techniques of molecular biology, microbiology, recombinant DNA technology and immunology which are known to those skilled in the art. Such techniques are explained fully in the literature. See for example the following references:

1. Maniatis, Fritsch and Sambrook, Molecular Cloning: A Laboratory Manual, 1982;
2. DNA Cloning, Vol. I and II, Glover, D. N., ed. 1985;
3. Oligonucleotide Synthesis, Gait, M. J., ed. 1984;
4. Nucleic Acid Hybridization, Hames, B. D. and Higgins, S. J. eds. 1986;
5. Animal Cell Culture, Freshney, R. K. ed. 1986;
6. Immobilized Cells and Enzymes, IRL Press, 1986;
7. Perbal, B. A Practical Guide to Molecular Cloning, 1984;
8. The Series, Methods In Enzymology, Colowick, S. and Naplan, N. eds. Academic Press Inc.;
9. Handbook of Experimental Immunology, Vol. I-IV, Weir, D. M and Blackwell, C. C. eds. 1986, Blackwell Scientific Publications.

I. Nucleic Acid Molecules of the Invention

The present invention includes a modified leukotoxin gene for the preparation of a modified leukotoxin protein.

The term "modified leukotoxin gene" as used herein means a nucleic acid sequence encoding a leukotoxin protein that has been modified to remove nucleic acid sequences that encode amino acids within a hydrophobic transmembrane domain of a full length leukotoxin protein.

The term "modified leukotoxin protein" means a leukotoxin protein that has been modified to remove amino acid sequences within a hydrophobic transmembrane domain of the full length leukotoxin. A modified leukotoxin can have amino acids deleted in one or more of the hydrophobic domains of the full length protein.

In one embodiment, the modified leukotoxin is derived from the full length or naturally occurring leukotoxin from M. haemolytica. The sequence of the full length leukotoxin protein of M. haemolytica is shown in FIG. 13 (SEQ.ID.NO.:5). Three hydrophobic domain regions are present in the sequence and are found at the following positions: domain 1—amino acids 230-250; domain 2—amino acids 280-320; and domain 3—amino acids 360-400. In one embodiment, the modified leukotoxin protein has a deletion of at least one of the hydrophobic domains, more preferably at least two of the hydrophobic domains and most preferably all three of the hydrophobic domains.

The invention also includes modified leukotoxin proteins based on leukotoxins from other species including Actinobacillus actinomycetemcomitans (GenBank Accession nos. A37205, AAA21922, CAA34731, CAA34730, P16462); Pasteurella suis (U.S. Pat. No. 5,559,008); Synecnocystis sp. (BAA18765); and other P. haemolytica serotypes (T10: A35254, P55117; A11: P55118; T3: P55116; and 5943B: P55123). The hydrophobic domains of a leukotoxin can be determined by one of skill in the art for example by comparing the sequence to the leukotoxin of M. haemolytica shown in FIG. 13 and matching the hydrophobic regions or by preparing a Kyte-Doolittle hydropathy plot of the leukotoxin protein. In some instances, the hydrophobic domains are identified in the published sequences. For example, the hydrophobic regions of *A. actinomycetemcomitans* may be found in the above referenced GenBank Accession nos. or in J. Biol. Chem. 264(26), 15451-15456, 1989.

The modification or deletion in the modified leukotoxin protein should be sufficient to render the modified protein incapable of inserting into the membrane of target cells rendering it devoid of toxic activity.

Preferably, the modified leukotoxin has at least 20 amino acids, more preferably from 50 to 500 amino acids deleted from one or more hydrophobic domains. The modified leukotoxin protein may additionally have deletions in other portions of the protein such as in the N terminus or C terminus outside of the hydrophobic domains.

Advantageously, the modified leukotoxin protein when prepared by recombinant means is produced at levels that are higher than when the full length leukotoxin protein is prepared under the same conditions. The modified leukotoxin protein retains its ability to generate an immune response. In particular, the modified leukotoxin protein can induce an antibody response when used to immunize an animal.

Generally, a modified leukotoxin gene can be produced by an in-frame deletion of amino acids within the hydrophobic transmembrane domains of the full length leukotoxin gene, lkta. Accordingly, the present invention provides a purified and isolated nucleic acid molecule comprising a sequence encoding a modified leukotoxin wherein the modification comprises the removal of nucleic acid sequences encoding amino acids within at least one transmembrane domain of the full length leukotoxin gene.

The term "isolated" refers to a nucleic acid substantially free of cellular material or culture medium when produced by recombinant DNA techniques, or chemical precursors, or other chemicals when chemically synthesized The term "nucleic acid sequence" refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thio-alkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

In one embodiment, the inventors have prepared a modified leukotoxin protein by deleting the nucleic acid sequences that encode the entire region containing the three hydrophobic domains in the leukotoxin from *M. haemolytica*. The hydrophobic transmembrane domains, spanning from about amino acid number 50 to about amino acid number 400, of the full length leukotoxin from *M. haemolytica* are clearly visible in the Kyte-Doolittle hydropathy plot shown in FIG. 3. The in-frame deletion may be performed by the digestion of lktA using the appropriate restriction enzyme or enzymes and re-ligation of the two external pieces using standard techniques. The nucleic acids coding for the hydrophobic domains of leukotoxin are located approximately between about position 618 and about position 1653 in the lktA sequence (see Lo, R. Y. C. et al. Infect. and Immun. 1987, 55:1987-1996). The use of any restriction enzyme or enzymes that result in the removal of this region in lkta is within the scope of the present invention. In a preferred embodiment of the invention, the restriction enzyme is NaeI. After deletion of the in-frame fragment, the remaining lkta gene (named lktAΔN) codes for a modified protein of approximately 66 kDa, hence the name Lkt-66. The nucleic acid sequence of a modified leukotoxin gene obtained using NaeI and the corresponding amino acid sequence of the modified leukotoxin are shown in FIGS. 1A and 1B (or SEQ.ID.NO.:1) and FIGS. 2A and 2B (or SEQ.ID.NO.:2), respectively. The invention extends to cover nucleic acid and amino acid sequences substantially homologous and functionally equivalent to those shown in FIGS. 1A and 1B and FIGS. 2A and 2B, respectively as well as analogs, derivatives and fragments thereof.

Accordingly, the present invention provides an isolated nucleic acid molecule having a sequence which encodes a modified leukotoxin having an amino acid sequence as shown in FIGS. 2A and 2B (or SEQ.ID.NO.:2).

Preferably, the purified and isolated nucleic acid molecule comprises:

(a) a nucleic acid sequence as shown in FIGS. 1A and 1B (or SEQ.ID.NO.:1), wherein T can also be U;

(b) a nucleic acid sequences complementary to (a);

(c) a nucleic acid sequence which has substantial sequence homology to (a) or (b);

(d) a fragment of (a) to (c) that is at least 15 bases, preferably 20 to 30 bases, and which will hybridize to (a) to (c) under stringent hybridization conditions;

(e) a nucleic acid molecule differing from any of the nucleic acids of (a) to (c) in codon sequences due to the degeneracy of the genetic code; or (f) a nucleic acid sequence that is an analog of a sequence (a) to (e).

In another embodiment, the inventors have prepared a modified leukotoxin protein wherein the N-terminal end (up until about amino acid number 450) and 52 amino acids from the C-terminal end of the full length leukotoxin protein from *M. haemolytica*, have been deleted. The deletion in the N-terminal end includes the 3 hydrophobic domains of the leukotoxin as illustrated in FIG. 13 (SEQ.ID.NO.:5). This modified leukotoxin protein is termed Lkt 50 and its preparation is more fully described in Example 2. The nucleic acid sequence of the gene encoding Lkt 50 is shown in FIG. 11. The amino acid sequence of Lkt 50 is shown in FIG. 12 (SEQ.ID.NO.:4).

Accordingly, the present invention provides an isolated nucleic acid molecule having a sequence which encodes a modified leukotoxin having an amino acid sequence as shown in FIG. 12 (SEQ.ID.NO.:4).

Preferably, the purified and isolated nucleic acid molecule comprises:

(a) a nucleic acid sequence as shown in FIG. 11 (SEQ.ID.NO.:3), wherein T can also be U;

(b) a nucleic acid sequences complementary to (a);

(c) a nucleic acid sequence which has substantial sequence homology to (a) or (b);

(d) a fragment of (a) to (c) that is at least 15 bases, preferably 20 to 30 bases, and which will hybridize to (a) to (c) under stringent hybridization conditions;

(e) a nucleic acid molecule differing from any of the nucleic acids of (a) to (c) in codon sequences due to the degeneracy of the genetic code; or (f) a nucleic acid sequence that is an analog of a sequence (a) to (e).

It will be appreciated that the invention also includes nucleic acid molecules encoding homologs, analogs, derivatives and fragments of modified leukotoxin proteins of the invention wherein such homologs, analogs, derivatives and fragments have the same utility as the modified leukotoxin proteins.

In particular, the invention includes nucleic acid molecules comprising nucleic acid sequences having substantial sequence homology with the nucleic acid sequences as shown in FIGS. 1A and 1B or 11 and fragments thereof. The term "sequences having substantial sequence homology" means those nucleic acid sequences which have slight or inconsequential sequence variations from these sequences, i.e., the sequences function in substantially the same manner to produce functionally equivalent proteins. The variations may be attributable to local mutations or structural modifications.

Two nucleotide sequences are "substantially homologous" when at least about 80% preferably at least about 90% and most preferably at least about 95% of the nucleotides or amino acids match over a defined length of the molecule. Nucleotide sequences that are substantially homologous can be identified in a Southern hybridization experiment under, for example, stringent hybridization conditions, as defined below.

Another aspect of the invention provides a nucleic acid molecule, and fragments thereof having at least 15 bases, which hybridize to nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

Isolated and purified nucleic acid molecules having sequences which differ from the nucleic acid sequence shown in FIGS. 1A and 1B or 11 due to degeneracy in the genetic code are also within the scope of the invention. Such nucleic acids encode functionally equivalent proteins but differ in sequence from the above mentioned sequences due to degeneracy in the genetic code.

The term "a nucleic acid sequence which is an analog" means a nucleic acid sequence which has been modified as compared to the sequence of FIGS. 1A and 1B or 11 wherein the modification does not alter the utility of the sequence (i.e. does not insert into target cells and is useful in vaccine formulations) as described herein. The modified sequence or analog may have improved properties over the sequence shown in FIGS. 1A and 1B or 11. One example of a modification to prepare an analog is to replace one of the naturally occurring bases (i.e. adenine, guanine, cytosine or thymidine) of the sequence shown in FIGS. 1A and 1B or FIG. 11 with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in FIGS. 1A and 1B or FIG. 11. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a novel protein of the invention may be accomplished by expressing the cDNA in an appropriate host cell by standard techniques, and testing the activity of the protein using the methods as described herein. A cDNA having the activity of a novel protein of the invention so isolated can be sequenced by standard techniques, such as dideoxynucleotide chain termination or Maxam-Gilbert chemical sequencing, to determine the nucleic acid sequence and the predicted amino acid sequence of the encoded protein.

II. Novel Proteins of the Invention

The invention further broadly contemplates an isolated modified leukotoxin protein wherein the modification comprises the removal of amino acids within a hydrophobic transmembrane domain of a full length leukotoxin protein. The modified leukotoxin is incapable of inserting into target membranes making it very useful in the preparation of a vaccine. The inventors have surprisingly shown that the modified leukotoxin protein of the invention is much more stable than the full length leukotoxin protein. When prepared using recombinant DNA techniques, the yield of the modified leukotoxin protein is at least 50 times higher than that of the full length leukotoxin protein.

In one embodiment of the invention, an isolated protein is provided which has the amino acid sequence as shown in FIGS. 2A and 2B.

In another embodiment of the invention, an isolated protein is provided which has the amino acid sequence as shown in FIG. 12.

Within the context of the present invention, a protein of the invention may include various structural forms of the primary protein which remain immunogenic. For example, a protein of the invention may be in the form of acidic or basic salts or in neutral form. In addition, individual amino acid residues may be modified by oxidation or reduction.

In addition to the amino acid sequence (FIGS. 2A and 2B or FIG. 12), the protein of the present invention may also include analogs, homologs, derivative and fragments of the modified leukotoxin proteins as described herein.

Analogs of the protein having the amino acid sequence shown in FIGS. 2A and 2B or FIG. 12, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences shown in FIGS. 2A and 2B or FIG. 12. Amino acid insertions may consist of single amino acid residues or sequential amino acids ranging from 2 to 15 amino acids in length. For example, amino acid insertions may be used to enhance the immunogenicity of the protein.

Deletions may consist of the removal of one or more amino acids, or discrete portions from the amino acid sequence shown in FIGS. 2A and 2B or FIG. 12. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences.

Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence shown in FIGS. 2A and 2B or FIG. 12 as described herein. Such homologs are proteins whose amino acid sequences are comprised of amino acid sequences that hybridize under stringent hybridization conditions (see discussion of stringent hybridization conditions herein) with a probe used to obtain a protein of the invention. Homologs of a protein of the invention will have the same regions which are characteristic of the protein. A homologous protein includes a protein with an amino acid sequence having at least 80%, preferably 90%, most preferably 95% identity with the amino acid sequence as shown in FIGS. 2A and 2B or FIG. 12.

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes derivatives of the proteins of the invention. "Derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The present invention also includes a protein of the invention conjugated with a selected protein, or a selectable marker protein to produce fusion proteins.

The proteins of the invention (including homologs, analogs, etc.) may be prepared using recombinant DNA methods. In particular, nucleic acid molecules of the present invention having a sequence which encodes a modified leukotoxin protein of the invention may be incorporated according to procedures known in the art into an appropriate expression vector or replicon which ensures good expression of the protein. Accordingly, the invention provides a method for the production of a modified leukotoxin in a host cell comprising:

a) introducing into the host cell a chimeric nucleic acid sequence molecule comprising in the 5' to 3' direction of transcription:

1) a first nucleic acid sequence capable of regulating transcription in said host cell operatively linked to;

2) a second nucleic acid sequence encoding a modified leukotoxin protein operatively linked to;

3) a third nucleic acid sequence capable of terminating transcription in said host cell; and b) culturing said host cell under suitable conditions to allow said cell to express the modified leukotoxin protein.

The chimeric nucleic acid is prepared in a vector. Numerous cloning vectors are known to those skilled in the art and the selection of an appropriate cloning vector is a matter of choice. The term vector is meant to mean a replicon, such as a plasmid, phage or cosmid, to which another DNA segment may be attached so as to bring about the replication of the attached segment. Examples of recombinant DNA vectors for cloning, and host cells which they can transform, include the bacteriophage lambda (*E. coli*), pTTQ18 (*E. coli*), pBR322 (*E. coli*), pACYC177 (*E. coli*), pKT230 (gram negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), Ylp5 (*Saccharomyces*), Ycp19 (*Saccharomyces*), bovine papilloma virus (mammalian cells) and pBl121 (plant).

The coding sequence for the modified leukotoxin can be placed under the control of a promoter, ribosome binding site (for bacterial expression) and, optionally, an operator (collectively referred to herein as "control elements"), so that the DNA sequence encoding the protein is transcribed into mRNA in the host cell transformed by a vector containing this expression construct. The coding sequence may or may not contain a signal peptide or a leader sequence. In one embodiment, the expression of modified gene is regulated by the inducible tac promoter.

In addition to control sequences, it may be desirable to add regulatory sequences which allow for regulation of the expression of the bacterial antigen sequences relative to the growth of the host cell. Regulatory sequences are known to those skilled in the art, and examples include those which cause the expression of a gene to be turned on or off in response to a chemical or physical stimulus, including the presence of a regulatory compound. Other types of regulatory elements may be present in the vector, for example, enhancer sequences. The subject proteins may also be expressed in the form of a fusion protein, wherein a heterologous amino acid sequence is expressed at the N-terminal or C-terminal.

An expression vector is constructed so that the particular coding sequence is located in the vector with the appropriate regulatory sequences, the positioning and orientation of the coding sequence with respect to the control sequences being such that the coding sequence is transcribed under the control of the control sequences (i.e. RNA polymerase which binds to the DNA molecule at the control sequences transcribes the coding sequence). Modification of the sequences encoding the particular protein of interest may be desirable to achieve this end. For example, in some cases it may be necessary to modify the sequence so that it may be attached to the control sequences with the appropriate orientation, i.e., to maintain the reading frame. The control sequences and other regulatory sequences may be ligated to the coding sequence prior to insertion into a vector, such as the cloning vectors described above. Alternatively, the coding sequence can by cloned directly into an expression vector which already contains the control sequences and an appropriate restriction site.

In some cases, it may be desirable to add sequences which cause the secretion of the protein from the host organism. Such secretion sequences may be located in the same vector or in a separate vector. When *E. coli* is the host, the use of a separate vector, for example, the plasmid pWAM716, which codes for the hlyB/D secretion functions, is preferred.

Depending on the expression system and the host selected, the protein of the present invention may be produced by growing host cells, transformed by an expression vector described above, under conditions whereby the protein of interest is expressed. The protein may be then isolated from the host cells and purified. If the expression system secretes the protein into the growth media, the protein is purified directly from the media. If the protein is not secreted, it is isolated from cell lysates. The selection of the appropriate growth conditions and recovery methods are within the skill of the art.

The host cell may be selected from a wide range of host cells including plants, bacteria, yeasts, insects and mammals. In one embodiment the host cell is a plant cell. The plant may be selected from various plant families including Brassicaceae, Compositae, Euphorbiaceae, Leguminosae, Linaceae, Malvaceae, Umbilliferae, Graminae, Nicotiana and Trifolium spp. Particular types of plants that may be used to prepare the modified leukotoxin protein include tobacco (*Nicotiana tobacum*), white clover (*Trifolium repens*), soybean (*Glycine max*), rapeseed (*Brassica napus, Brassica campestris*), sunflower (*Helianthus annuus*), cotton (*Gossypium hirsutum*), corn (*Zea mays*), alfalfa (*Medicago sativa*), wheat (*Triticum* sp.), barley (*Hordeum vulgare*), oats (*Avena sativa* L.), sorghum (*Sorghum bicolor*), *Arabidopsis thaliana*, potato (*Solanum* sp.), flax/linseed (*Linum usitatissimum*), safflower (*Carthamus tinctorius*), oil palm (*Eleais guineeis*), groundnut (*Arachis hypogaea*), Brazil nut (*Bertholletia excelsa*) coconut (*Cocus nucifera*), castor (*Ricinus communis*), coriander (*Coriandrum sativum*), squash (*Cucurbita maxima*), jojoba (*Simmondsia chinensis*) and rice (*Oryza sativa*).

Accordingly, the invention provides a method for the production of a modified leukotoxin in a plant comprising:

a) introducing into a plant cell a chimeric nucleic acid sequence molecule comprising in the 5' to 3' direction of transcription:

1) a first nucleic acid sequence capable of regulating transcription in said plant cell operatively linked to;
2) a second nucleic acid sequence encoding a modified leukotoxin protein operatively linked to;
3) a third nucleic acid sequence capable of terminating transcription in said plant cell; and b) growing said plant cell into a mature plant wherein said plant expresses the modified leukotoxin protein.

The preparation of the modified leukotoxin protein in plants offers a significant advantage as the plant can be consumed directly by the animal as a vaccine. The modified leukotoxin does not necessarily have to be isolated from the plant.

The proteins of the present invention may also be produced by chemical synthesis such as solid phase peptide synthesis. Such methods are known to those of skill in the art as discussed above for the synthesis of nucleic acids.

The proteins of the present invention (or homologs, analogs, derivatives and fragments thereof) may be used to produce both polyclonal or monoclonal antibodies. Antibodies that bind a protein of the invention and its homologs can be prepared using techniques known in the art such as those described by Kohler and Milstein, Nature, 1975, 256:495 and in U.S. Pat. Nos. RE 32,011, 4,902,614, 4,543,439 and 4,411, 993. (See also Monoclonal Antibodies, Hybridomas: A New Dimension in Biological Analyses, Kennett, McKearn and Bechtol, eds. Plenum Press, 1980 and AntibodiesL A Laboratory Manual, Harlow and Lane, eds. Cold Spring Harbor Laboratory Press, 1988).

Within the context of the present invention, antibodies are understood to include monoclonal antibodies, polyclonal antibodies, antibody fragments (e.g. Fab and F(ab( )$_2$) and recombinantly produced binding partners. Antibodies are understood to be reactive against the protein encoded by the modified leukotoxin gene of *M. haemolytica* and its homologs if they bind to the receptor with an affinity of greater than or equal to $10^{-6}$ M.

Polyclonal antibodies may be readily generated by one of ordinary skill in the art from a variety of warm-blooded animals such as horses, cows, various fowl, rabbit, mice or rats. Briefly, a modified leukotoxin protein or a homolog, analog, derivative or fragment thereof, may be used through intraperitoneal, intramuscular, intraocular, or subcutaneous injections, in conjunction with an adjuvant such as aluminum hydroxide or saponin. Following several booster immunizations, samples of serum are collected and tested for reactivity to the protein. Once the titer of the animal has reached a plateau in terms of reactivity to the receptor protein, larger quantities of antisera may be obtained by weekly bleedings, or by exsanguinating the animal.

Monoclonal antibodies may also be generated using conventional techniques. Generally, hybridoma cell lines are prepared by a process involving the fusion under appropriate conditions of an immortalizing cell line and spleen cells from an animal appropriately immunized to produce the desired antibody. Immortalizing cell lines may be murine in origin however, cell lines of other mammalian species may be employed including those of rat, bovine, canine, human origin and the like. The immortalizing cell lines are most often of tumor origin, particularly myeloma cells, but may also include normal cells transformed with, for example, Epstein Barr Virus. Any immortalizing cell may be used to prepare the hybridomas of the present invention.

Antibody producing cells may be employed as fusion partners such as spleen cells or peripheral blood lymphocytes. The animal from which the cells are to be derived may be immunized at intervals with a protein of the invention or its homolog.

The immortalizing cells and lymphoid cells may be fused to form hybridomas according to standard and well-known techniques employing polyethylene glycol as a fusing agent. Alternatively, fusion may be accomplished by electrofusion.

Hybridomas are screened for appropriate monoclonal antibody secretion by assaying the supernatant or protein purified from the ascites for reactivity with a protein of the invention or its homolog.

The monoclonal antibodies produced by the hybridoma cell lines of the invention are also part of the present invention. It is understood that immunoglobulins may exist in acidic, basic or neutral form depending on their amino acid composition and environment, and they be found in association with other molecules such as saccharides or lipids. The monoclonal antibodies produced by hybridoma cell lines of the invention may be directed to one or more epitope of a modified leukotoxin protein of the invention or homologs thereof. Any characteristic epitope associated with a modified leukotoxin protein or its homolog may provide the requisite antigenic determinant. It is contemplated that monoclonal antibodies produced by the hybridoma cell lines fall within the scope of the present invention so long as they remain capable of selectively reacting with peptides from the modified leukotoxin protein or its homolog. Monoclonal antibodies are useful in purification, using immunoaffinity techniques, of the proteins of the invention which they are directed against.

III. Therapeutic Applications

As mentioned previously, the modified leukotoxin proteins of the invention are useful as vaccines as the modified leukotoxin does not insert into target cells and does not display toxic activity. Accordingly, a modified leukotoxin gene or protein of the invention may be used to treat and prevent diseases caused bacteria that release the full length or naturally occurring leukotoxin or related toxins. As an example, a modified leukotoxin protein derived from a *Mannheimia* leukotoxin may be used to treat diseases or conditions caused by *Mannheimia* infections such as respiratory disease. The modified leukotoxin derived from *Mannheimia* may also be useful in treating diseases or conditions caused by other bacteria when the modified leukotoxin shares epitopes that would cross react with the leukotoxin from the other bacteria.

Accordingly, the present invention provides a method of treating or preventing a condition associated with a leukotoxin, such as a *Mannheimia haemolytica* infection, comprising administering an effective amount of a modified leukotoxin gene or protein to an animal in need thereof. The invention also includes a use an effective amount of the modified leukotoxin gene or protein to treat or prevent a condition associated with a leukotoxin. The invention further includes a use of a modified leukotoxin gene or protein to prepare a medicament to treat or prevent a condition associated with a leukotoxin.

Administration of an "effective amount" of a modified leukotoxin gene or protein of the present invention is defined as an amount of the gene or protein, at dosages and for periods of time necessary to achieve the desired result. For example, an effective amount of a substance may vary according to factors such as disease state, age, sex, and weight of the recipient, and the ability of the substance to elicit a desired immune response in the recipient animal. Dosage regima may be adjusted to provide an optimum therapeutic response.

The term "animal" as used herein includes all members of the animal kingdom, preferably a ruminant, more preferably cattle.

A modified leukotoxin protein of the invention or a homolog, analog, derivative or fragment thereof may be administered as a vaccine composition to prevent or treat respiratory disease in an animal, in particular, a ruminant. In particular, a protein of the invention may be used to prevent or ameliorate respiratory disease associated with a *Mannheimia* species in an animal, preferably a ruminant.

Animals can be immunized with the compositions of the present invention by administration of the modified leukotoxin protein or a homolog, analog, derivative or fragment thereof. Prior to immunization, it may be desirable to increase the immunogenicity of the modified leukotoxin protein. This can be accomplished in any one of several ways known to those skilled in the art. For example, the protein may be administered linked to a carrier. For example, a fragment may be conjugated with a macromolecular carrier. Suitable carriers are typically large, slowly metabolized macromolecules such as: proteins (for example, serum albumins, keyhole limpet hemocyanin, immunoglobulin molecules, thyroglobulin, ovalbumin and the like) polysaccharides (for example, sepharose, agarose, cellulose, cellulose beads and the like) polymeric amino acids (for example, polyglutamate, polylysine and the like), amino acid co-polymers and inactive virus particles.

The proteins may be used in their native form or their functional group content may be modified by, for example, succinylation of lysine residues or reaction with Cys-thiolactone. A sulfhydryl group may also be incorporated into the carrier or the protein, for example by reaction of amino functions with 2-iminothiolane or the N-hydroxysuccinimide ester of 3-(4-dithiopyridyl) propionate. Suitable carriers may also be modified to incorporate spacer arms (such as hexamethylene diamine or other bifunctional molecules of similar size) for attachment of peptides.

Other suitable carriers for the proteins of the invention include VP6 polypeptides of rotaviruses, or functional fragments thereof as disclosed in U.S. Pat. No. 5,071,651. Also useful is a fusion product of a viral protein and the epitope of interest made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention, or antigenic fragment or homolog thereof, may be coupled to erythrocytes, preferably the subject's own erythocytes. Methods of coupling peptides to proteins or cells are known to those skilled in the art.

The modified leukotoxin protein, or homolog, analog, derivative or fragment thereof, may be administered alone or mixed with a pharmaceutically acceptable vehicle or excipient. Typically vaccines are prepared as injectables, either as liquid solutions or suspensions. Solid forms suitable for solution or suspension in liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include, for example, muramyl dipeptides, pyridine, aluminum hydroxide, oils, saponins and other substances known in the art. The preparation of such dosage forms is well known to those skilled in the art (see for e.g. Remington's Pharmaceutical Sciences, Mack Publishing Company, Easton, Pa. USA, 1985).

Additional vaccine formulations which are suitable for other modes of administration include suppositories and, in some cases, aerosol, intranasal and oral formulations. For suppositories, the vehicle composition will include traditional binders and carriers, such as polyalkaline glycols or triglycerides. Such suppositories may be formed from mixtures of active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate and the like. These oral vaccine compositions may be taken in the form of solutions, suspensions, tablets, pills, capsules, sustained release formulations, or powders and contain from about 10% to about 95%, preferably about 25% to about 70%, of the active ingredient.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject protein by the nasal mucosa.

The modified leukotoxin proteins or homologs, analogs, derivatives or fragments thereof, may be formulated into vaccine compositions in either neutral or salt forms. Pharmaceutically acceptable salts include acid addition salts formed with inorganic acids, such as, for example, hydrochloric or phosphoric acids, or organic acids, such as, for example, acetic, oxalic, tartaric, mandelic acids and the like. Basic addition salts may also be formed from free carboxyl groups and may be derived from inorganic bases such as, for example, sodium, potassium, ammonium, calcium or ferric hydroxides, or organic bases such as, for example, isopropylamine, trimethylamine, 2-ethylaminoethanol, histidine, procaine and the like.

To immunize the subject, the protein of interest, or homologs, analogs, derivatives or fragments thereof, may be administered parenterally, usually by intramuscular injection in an appropriate vehicle, as described above. Other modes of administration, such as subcutaneous, intravenous and intranasal delivery, are also acceptable. Injectable vaccine formulations will contain an effective amount of the active ingredient in a vehicle, the exact amount being readily determined by a person skilled in the art. The active ingredient may typically range from about 1% to about 95% (w/w) of the composition, or even higher or lower, if appropriate. The quantity to be administered depends on the animal to be treated, the capacity of the animal's immune system to synthesize antibodies, and the degree of protection desired. Effective dosages can readily be established by one skilled in the art through routine trials establishing dose response curves. The subject is immunized by administration of the antigenic protein, or homolog, analogs, derivatives or fragments thereof, in at least one dose, and preferably two doses. Moreover, the subject may be administered as many doses as is required to maintain a state of immunity to the respiratory disease.

It is envisaged that the modified leukotoxin proteins of the invention, or homologs, analogs, derivatives or fragments thereof, may be used in a combination vaccine. For example, vaccines comprising proteins or polypeptides expressing other antigens of *M. haemolytica* (such as those described in U.S. Pat. No. 5,871,750, incorporated herein by reference) or proteins or polypeptides expressing antigens of other diseases affecting the animal.

As another aspect of the present invention, vaccine compositions are provided comprising a pharmaceutically acceptable carrier and a nucleic acid sequence encoding the modified leukotoxin protein, wherein the modification comprises the removal of nucleic acid sequences encoding amino acids within the hydrophobic transmembrane domains of the full length leukotoxin protein, or a nucleic acid sequence substantially homologous and functionally equivalent thereto. The nucleic acid sequence is operably linked to regulatory sequences and inserted into a suitable vector so that it is capable of being expressed in vivo in the animal. The insertion of the nucleic acid sequences of the invention into suitable vectors has been previously described herein. Suitable vectors for administering the nucleic acid as a vaccine include retroviral vectors, adenoviral vectors and DNA virus vectors. The vaccine vector containing a nucleic acid molecule of the invention can either be (a) administered directly into an animal or (b) used to transform host cells in vitro and the transformed host cells can be administered to an animal. For the former application, the vector may be administered in admixture with suitable carriers as described hereinabove for the leukotoxin protein vaccine. In a specific embodiment, the transformed host cell is a plant cell wherein the transformed plant can be fed directly to animals for immunization.

The present invention will be further illustrated in the following examples. However, it is to be understood that these examples are for illustrative purposes only, and should not be used to limit the scope of the present invention in any manner.

EXAMPLES

Example 1

The modified leukotoxin gene lktAΔN was prepared by deleting the hydrophobic domains of the full length *M. haemolytica* leukotoxin gene containing nucleotides 618 to 1653. The nucleic acid sequence and amino acid sequence of lktAΔN is shown in FIGS. 1A and 1B and 2A and 2B, respectively. The lktAΔN was cloned into an expression plasmid (pTTQ18) which placed the regulation of expression under the inducible tac promoter. In the presence of another plasmid, pWAM716 which coded for the hlyB/D secretion functions, the rLkt is secreted into the supernatant of *E. coli* cultures for ease of recovery.

1. An *E. coli* strain that carries both plasmids, pLKTΔN and pWAM716, was used. As controls, *E. coli* carrying pWAM761 and pLKT60 (full length IktA); and *E. coli* carrying pWAM716 and pTTQ18 (no lktA gene) were also used as positive and negative controls respectively. All strains were maintained on LT supplemented with ampicillin (100 μg/ml) and chloroamphenicol (25 μg/ml) to select for the plasmids.
2. The following is the procedure for production and recovery of rLkt from the *E. coli* cultures:
   Step 1—Prepare overnight cultures in LT+ ampicillin (100 μg/ml)+chloramphenicol (25 μg/ml), 20 ml, 37° C.
   Step 2—Subculture overnight into 1 lit. LT+ampicillin+chloramphenicol (1/50), grow for 2 hr.
   Step 3—Induce with IPTG, final conc. 0.5 mM, grow for 1 hr.
   Step 4—Spin down cells in GSA rotor (12,000 rpm) 20 min., recover supernatant.
   Step 5—Concentrate supernatant app. 10× using Amicon PM10 filtration apparatus.
   Step 6—Dialyze concentrate against distilled water at 4° C. over 2 days with at least 5 changes of 10× vol. I used a membrane cut off of app. 50 kDa.
   Step 7—Lyophilize material, resuspend final powder in 2 ml distilled water.
3. The material prepared was injected into rabbits to produce antibodies. The antibodies were tested in Western immunoblots as well as toxin neutralization assays.
4. Gels and Western immunoblots:
   Samples: #3, full length Lkt-102
   #4, Lkt-66
   #5, negative sample, no lktA gene products
   B122, *M. haemolytica* A1 total proteins.

FIG. 4—Coomassie stained SDS-PAGE, note the faint 102 kDa band in sample #3 and the thick 66 kDa band in sample #4.

FIG. 5—Western immunoblot of a duplicate set of protein preparations immunostained with rabbit anti-Lkt102 (#3) and anti-Lkt66 (#4).

The anti-Lkt102 (#3) serum recognized the 102 kDa and 66 kDa bands as expected. The anti-66 (#4) serum also recognized the 102 kDa and the 66 kDa bands, indicating that the 66 kDa antigen stimulated antibody respond against the full length toxin.

5. Toxin neutralization

Rabbits #35, 36 and 37 were immunized with 102 kDa toxin, all produced toxin neutralization titers of 5 (½ⁿ), the prebleed tirers are 1, 0.5 and 2.

Rabbits #38 and 39 received the 66 kDa antigen. The toxin neutralization titers at the final bleed are 4 and 5 (prebleeds are 1 and 0) respectively. Therefore, the anti-66 serum also exhibit toxin neutralization activity similar to that of the anti-102.

Summary

A simple procedure for recovery of a modified leukotoxin (Lkt-66) from the culture supernatant of *E. coli* has been developed, wherein the modification comprises the removal of internal amino acids in the hydrophobic transmembrane domains of the full length leukotoxin protein. The yield of the modified protein was at least 50 times that of the full length leukotoxin rLkt-102 using the same procedure. The recovered materials contain the 66 kDa modified Lkt which can simulate an immune response in rabbits that recognize the authentic full length leukotoxin as well as toxin neutralization activity similar to that of the full length rLkt.

Example 2

1. Construction of lktA50

A derivative of Lkt66 (Lkt50) was made by further manipulation of the lktAΔN construct. PCR primers based on the lktA sequences at positions 1355 and 2705 were designed to amplify a fragment of 1.35 kbp. This fragment codes for all of the antigenic regions of Lkt66, lacking the N-terminal portion of the protein. The removal of the N-terminal amino acids of Lkt66 facilitates expression of the toxin derivative in plants. This construct, named lkt50 should produce a protein from amino acids 451 to 901 of the full length leukotoxin, for a molecular mass of 49.6 kDa, slightly less than half of the full length leukotoxin of 102 kDa. The corresponding amino acid regions are:

phe-leu-leu-asn-leu-asn-lys-glu-leu-gln . . . leu-ser-lys-val-val-asp-asn-tyr-glu- Note that the last amino acid glu is continued into the GFP protein.

2. Cloning of lkt50 into a Binary Vector

A binary vector pBINmgfp5-ER was used for cloning of the lkt50 fragment and introduction into plants by *Agrobacterium*-mediated transformation. The vector is a derivative of the plant transformation vector pB1121 (Clontech) and utilizes the cauliflower mosaic virus 35S promoter for expression. It contains mgfp5-ER which codes for a variant of the green fluorescent protein (GFP) for enhanced fluorescence (mGFP5). In addition, mgfp5-ER contains a signal peptide sequence and an endoplasmic reticulum (ER) retention sequence. PCR was carried out using specific primers designed to introduce the appropriate restriction sites for this manipulation. The PCR products were digested with the restriction enzyme and ligated into the plasmid, resulting in two constructs in which the positions of Lkt50 and mGFP5 were placed in front or after the other. These constructs should express a fusion protein of approximately 79 kDa.

3. Transient Expression of Plasmid Constructs in Tobacco

The two chimeric constructs, Lkt50-mGFP5 and mGFP5-Lkt50 inserted into the binary vectors were used to transform *Agrobacterium*. To rapidly assess if these constructs were able to direct the production of the fusion proteins in plants, they were first transiently expressed in tobacco by infiltration. Plasmid constructs containing promoterless mgfp5-ER and 35S-driven mgfp5-ER were used as controls for transient expression. Three to four days after infiltration, fluorescence was observed by microscopy only in plants injected with *Agrobacterium* transformed with 35S-mgfp5-ER. Plants infiltrated with *Agrobacterium* containing the promoterless construct showed no fluorescence. Little or no fluorescence was observed in the infiltrated regions of plants injected with *Agrobacterium* containing either Lkt50 construct. The infiltrated areas were excised and examined for the presence of recombinant fusion protein by Western immunoblot with rabbit anti-Lkt66 antibodies (FIG. 6). An immunoreactive band of approximately 79 kDa was present only when the Lkt50-mGFP5 construct was used. The size of the band corresponded to that predicted from the nucleotide sequence of the fusion protein. No specific immunostaining was observed with the control plasmids. Thus, it appeared that when mGFP5 was fused after Lkt50, the fusion was expressed in tobacco and resulted in the accumulation of a significant amount of recombinant protein. This construct was selected for the production of transgenic white clover lines.

4. Transgenic White Clover Expressing Lkt50-mGFP5

Transgenic clover lines expressing mGFP5 and Lkt50-mGFP5 were produced by *A. tumefaciens*-mediated transformation. PCR was used to confirm that the transgenes were present in transformed plants. By conventional fluorescence microscopy, mGFP5 fluorescence was easily detected in mGFP5 expressing plants. Consistent with the results obtained with transient expression, little to no fluorescence was observed in Lkt50-mGFP5 transformed plants. However, when these plants were further investigated using laser scanning confocal microscopy, green fluorescence was detected in clover transformed with both the mgfp5-ER and lkt50-mgfp5-ER constructs (FIG. 7). As expected, mGFP5 fluorescence was more intense than that observed for Lkt50-mGFP5. The pattern of green fluorescence observed in clover leaves was consistent with a localization of the recombinant protein in the endoplasmic reticulum. The cells contained large vacuoles which resulted in a distribution of fluorescence around the cell pheriphery. The fusion protein exhibited a perinuclear localization and was clearly excluded from the nucleus. A characteristic reticulate network was seen in some cells when the appropriate plane of focus was used.

Figure 8:
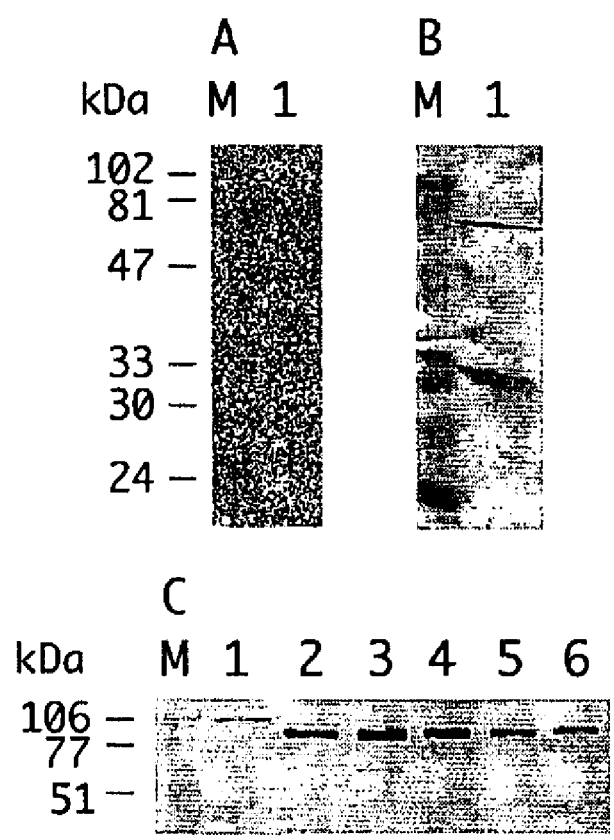
FIG. 8 shows the expression of Lkt50-mGFP5 in transgenic white clover. Expression of Lkt50-mGFP5 in transgenic white clover was analyzed by Western immunoblot. Duplicate blots of proteins extracted from one transgenic line were immunostained with either rabbit anti-Lkt66 antiserum (A, lane 1) or rabbit anti-GFP monoclonal (Clonetech) (B). Molecular sizes of the pre-stained SDS-PAGE standards (Bio-Rad) (A and B, lanes M) are indicated at the left. Both antibodies detected a protein of similar size, providing evidence that a Lkt50-mGFP5 fusion protein was indeed produced by the transgenic clover. In addition, the size of the fusion protein observed was close to the predicted size of 79 kDa as predicted from the nucleotide sequence. In panel C, The stability of Lkt50-mGFP5 recovered from clover was examined. Protein extracts were prepared from fresh transgenic clover (lane 2) or from clover dried for 1 day, 2 days, 3 days, or 4 days (lanes 3-6, respectively) were analyzed by Western immunoblot. The blot was probed with the rabbit anti-Lkt66 antiserum. A sample of M. haemolytica A1 supernatant containing full-length authentic Lkt was loaded in lane 1. Migration of molecular size markers (lane M) are shown on the left. After 4 days of drying at ambient temperatures, there does not appear to be significant degradation of the Lkt50-mGFP5 fusion protein.
Figure 9:
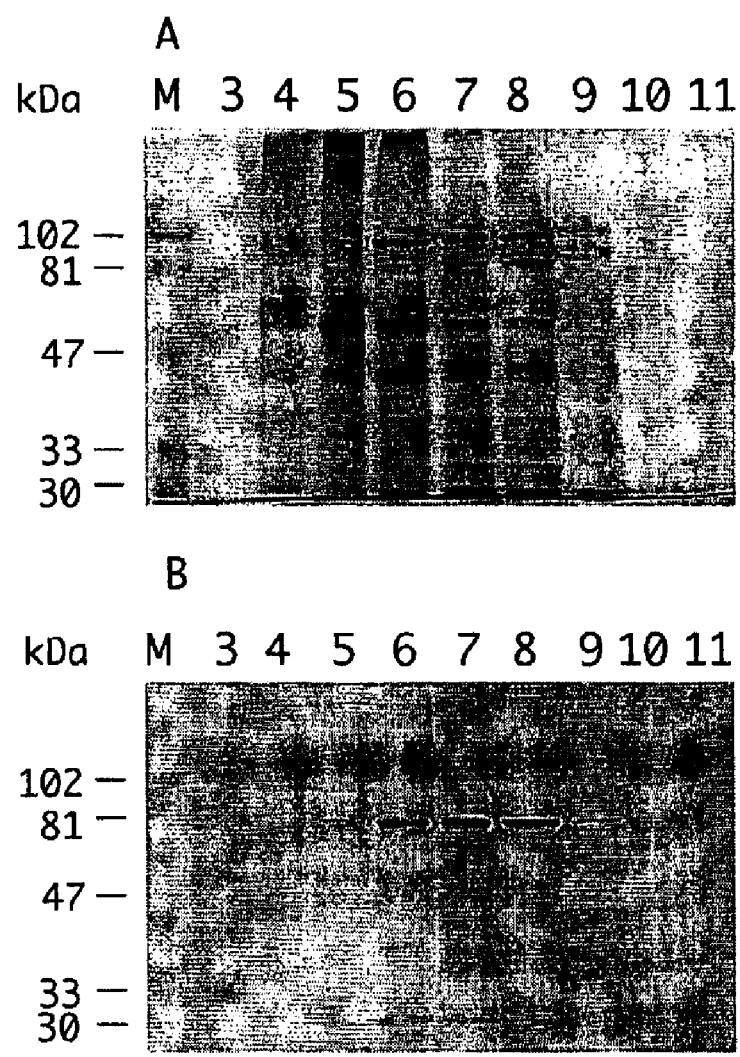
FIG. 9 shows the partial purification of Lkt50-mGFP5 for immunization. A supernatant was prepared from transgenic white clover and fractionated by chromatofocusing (Pharmacia). Column fractions were analyzed by SDS-PAGE (A) and Western immunoblot (B). The fraction numbers are indicated on the top and size markers (lanes M) are indicated at the left. These results show that Lkt50-mGFP5 (fractions 6, 7 and 8) can be separated from Rubisco (strongly staining band migrating at around 56 kDa) and other high molecular weight material (fractions 5 and 6).
Figure 10:
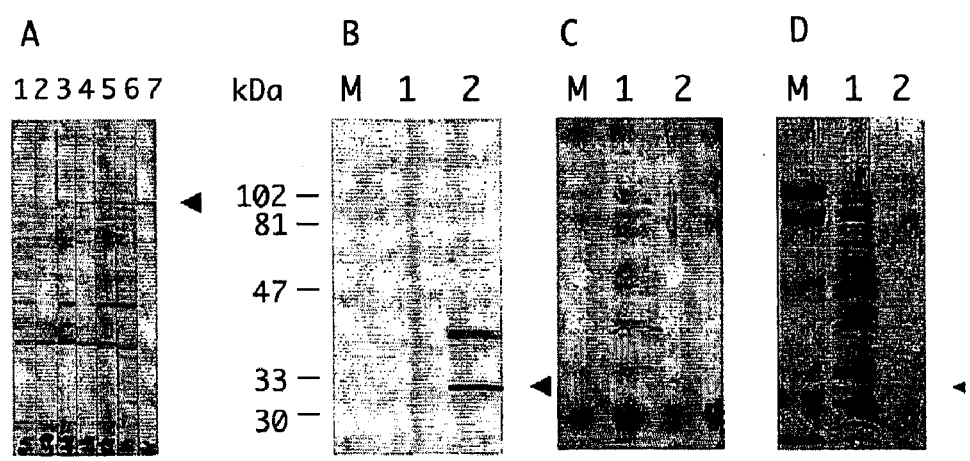
FIG. 10 shows the immunogenicity of Lkt50-mGF5 produced by white clover. (A) Rabbits (duplicate rabbits used for each treatment) were mock-immunized with saline and adjuvant (lanes 1 and 2) or immunized with chromatographic fractions enriched in Lkt50-mGFP5 (lanes 3 and 4) or a saline extract from transgenic clover (lanes 5 and 6). Immune sera were used to probe a total M. haemolytica A1 protein preparation blotted onto nitrocellulose membrane. The rabbit anti-Lkt-66 antiserum (lane 7) was used as positive control. Immune serum from all four rabbits immunized with Lkt50-mGFP5-containing fractions recognized a band migrating identically with that immunostained with anti-Lkt66 (lanes 3-7). Immune serum used in panel A lane 6 (rabbit 41) was analyzed to see if it cross reacts with wild type GFP (B and C). Triplicate blots (B, C and D) were prepared containing M. haemolytica A1 total protein preparation (lanes 1) and purified GFP (Clontech, lanes 2). Anti-GFP antibodies (B), anti-Lkt66 (C) and rabbit 41 immune serum (used in panel A, lane 6) (D) were used to probe the membranes. Rabbit 41 serum was able to detect mGFP5 (D, lane 2). These results suggest that the immune serum contain antibodies directed to both Lkt50 (A, lane 6 and D, lane 1) and GFP (D lane 2). Molecular size markers (B, C and D, lanes M) are as indicated on the left of panel B.

Expression of a recombinant fusion protein containing both Lkt66 and mGFP5 epitopes were confirmed by Western immunoblot analysis (FIGS. 8A & B). Both rabbit anti-Lkt66 and rabbit anti-GFP (Clontech) antibodies recognized a protein migrating at approximately 79 kDa. Preliminary scanning densitometric analysis of gels and the blots from one of the Lkt50-mGFP5 expressing clover lines (LKT6) suggested that the recombinant fusion protein constitute approximately 1% of the soluble proteins extracted from transgenic clover.

5. Stability of Lkt50-mGFP5

The stability of the Lkt50-mGFP5 fusion protein in harvested plants was examined. Transgenic clover expressing Lkt50-mGFP5 was harvested and allowed to dry at ambient temperatures. Protein extracts were prepared from plant material at different stages of drying and analyzed by Western immunoblot. After 4 days of drying, there did not appear to be significant degradation of the fusion protein as no lower molecular weight immunoreactive species was observed (FIG. 8C).

6. Immunogenicity of Lkt50-mGFP5 Produced from Transgenic White Clover

To determine if Lkt50-mGFP5 produced by clover was able to elicit an immune response, rabbits were immunized with either a saline extract or a Lkt50-mGFP5-enriched chromatographic fraction prepared from clover leaves.

The Lkt50-mGFP5-enriched fractions were produced by chromatofocusing (Pharmacia). A soluble protein extract prepared from transgenic clover was applied to a PBE 94 column and resulting fractions were analyzed by Western immunoblot (FIG. 9). Most of the fusion protein eluted in fractions 6 to 8 and these fractions were pooled for rabbit immunization. The fusion protein could be partially separated from ribulose-1,5-bisphosphate carboxylase/oxygenase (Rubisco), the most abundant protein in plant tissue, most of which eluted in fractions 5 and 6. Under the conditions used in the fractionation, Lkt50-mGFP5 was stable to degredation as indicated by the absence of lower molecular weight immunoreactive bands in the column fractions.

Sera were obtained from both pre-immunized and immunized rabbits and tested for the presence of antibodies by Western immunoblot (FIG. 10). All rabbits receiving fractions containing Lkt50-mGFP5 as antigen were able to produce antibodies directed against the authentic Lkt from *M. haemolytica* A1 (FIG. 10, lanes 3-6). Sera from mock-immunized rabbits (FIG. 10, lanes 1-2) or rabbits immunized with wild type white clover extract failed to immunostain Lkt (data not shown). Preimmune sera from all the rabbits also did not detect Lkt (data not shown).

Toxin neutralization assay was performed to determine if neutralizing antibodies were present in immune sera. All rabbits immunized with Lkt50-mGFP5 extracts as antigen exhibited neutralizing titres of up to a dilution of 1/16 (Table 1). Sera from mock-immunized rabbits (Table 1), from rabbits immunized with wild type white clover extract or preimmune sera) failed to neutralize at the lowest dilutions (data not shown).

While the present application has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Neutralizing titres of sera from rabbits immunized with rLkt-GFP fusion protein.

| Immunogen | Rabbit No. | Neutralizing Titre[a] Pre-immune | $2^{nd}$ bleed | $3^{rd}$ bleed | $4^{th}$ bleed |
|---|---|---|---|---|---|
| Lkt50-mGFP5 | 41 | 0 | 0 | 4 | 3.5 |
| (saline extract) | 42 | 0 | 0 | 1 | 1 |
| Lkt-mGFP5 | 43 | 0 | 0 | 1 | 1 |
| (column fraction) | 44 | 0 | 0 | 1.5 | 1 |
| Mock | 45 | 0 | 0 | 0 | 0 |
| | 46 | 0 | 0 | 0 | 0 |

[a]Values are mean reciprocal $\log_2$ serum dilutions giving at least 50% neutralization of toxicity

We claim:

1. An immunogenic composition comprising:
   (a) a modified leukotoxin comprising the amino acid sequence of SEQ ID NO: 2 prepared from a plant cell according to a method comprising:
   i) introducing into a plant cell a chimeric nucleic acid sequence molecule comprising in the 5' to 3' direction of transcription:
      1) a first nucleic acid sequence capable of regulating transcription in said plant cell operatively linked to;
      2) a second nucleic acid sequence, which encodes the modified leukotoxin, operatively linked to;
      3) a third nucleic acid sequence capable of terminating transcription in said plant cell; and
   ii) culturing said plant cell under conditions allowing for the expression of the modified leukotoxin and isolating the modified leukotoxin; and
   (b) a pharmaceutically acceptable carrier.

2. An immunogenic composition comprising:
   (a) a modified leukotoxin comprising the amino acid sequence of SEQ ID NO: 2 prepared from a plant according to a method comprising:
   i) introducing into a plant cell a chimeric nucleic acid sequence molecule comprising in the 5' to 3' direction of transcription:
      1) a first nucleic acid sequence capable of regulating transcription in said plant cell operatively linked to;
      2) a second nucleic acid sequence, which encodes the modified leukotoxin, operatively linked to;
      3) a third nucleic acid sequence capable of terminating transcription in said plant cell; and ii) regenerating said plant cell into a mature plant wherein said plant expresses the modified leukotoxin; and
(b) a pharmaceutically acceptable carrier.

3. The immunogenic composition of claim 1 wherein the modified leukotoxin consists of the amino acid sequence of SEQ ID NO: 2.

4. The immunogenic composition of claim 2 wherein the modified leukotoxin consists of the amino acid sequence consisting of SEQ ID NO: 2.

* * * * *